(12) United States Patent
Hsu et al.

(10) Patent No.: US 6,959,212 B2
(45) Date of Patent: Oct. 25, 2005

(54) SYSTEM AND METHOD FOR ARRHYTHMIA DISCRIMINATION

(75) Inventors: William Hsu, Circle Pines, MN (US); Joseph Martin Smith, St. Louis, MO (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 504 days.

(21) Appl. No.: 10/014,933

(22) Filed: Oct. 22, 2001

(65) Prior Publication Data

US 2002/0091333 A1 Jul. 11, 2002

Related U.S. Application Data

(63) Continuation of application No. 09/248,800, filed on Feb. 12, 1999, now Pat. No. 6,308,095.

(51) Int. Cl.[7] .............................................. A61B 5/0402
(52) U.S. Cl. ....................................................... 600/518
(58) Field of Search ................................. 600/516–518, 600/521; 607/14, 5

(56) References Cited

U.S. PATENT DOCUMENTS

| | | | | |
|---|---|---|---|---|
| 4,023,564 A | 5/1977 | Valiquette et al. | ...... | 128/206 A |
| 4,336,810 A | 6/1982 | Anderson et al. | .......... | 128/702 |
| 4,531,527 A | 7/1985 | Reinhold, Jr. et al. | ...... | 128/696 |

(Continued)

FOREIGN PATENT DOCUMENTS

| | | | | |
|---|---|---|---|---|
| DE | 4405827 | 6/1995 | ......... | A61B/5/0402 |
| EP | 0469817 | 2/1992 | .......... | A61N/1/362 |
| EP | 0506230 | 9/1992 | .......... | A61N/1/362 |
| EP | 0554208 | 8/1993 | ......... | A61B/5/0452 |
| EP | 0711531 | 5/1996 | ......... | A61B/5/0452 |
| EP | 0776631 | 11/1996 | ......... | A61B/5/0452 |
| EP | 0848965 | 6/1998 | ............ | A61N/1/37 |
| WO | 97/39681 | 10/1997 | .......... | A61B/5/046 |
| WO | 98/53879 | 12/1998 | ............ | A61N/1/39 |

OTHER PUBLICATIONS

Duru, Firat, et al., "The Potential for Inappropriate Ventricular Tachycardia Confirmation Using the Intracardiac Electrogram (EGM) Width Criterion", *PACE*, vol. 22, 1999, (Jul. 1999), 1039–1046.

Grady, Thomas A., et al., "Prognostice Significance of Exercise–Induced Left Bundle–Branch Block", *JAMA*, vol. 279, No. 2, Jan. 14, 1998, 153–156.

Kinoshita, Shinji , et al., "Transient Disapperance of Complete Right Bundle Branch (BBB) During Excercise", *Journal of Electrocardiology*, vol. 29, No. 3, 1996, 255–256.

IEEE, "Microcomputer–Based Telemetry System for ECG Monitoring", *IEEE Proc. of the Ann. Int'l Conf. of the Engineering in Medicine and Biology Society*, vol. Conf. 9, XP000015425, (1987), 1492–193.

Thompson, Julie , "Template Based AV/VA Interval Comparison for the Discrimination of Cardiac Arrhythmia", U.S. Appl. No. 10/844,475, filed May 12, 2004 33 pgs.

*Primary Examiner*—Jeffrey R Jastrzab
(74) *Attorney, Agent, or Firm*—Schwegman, Lundberg, Woessner & Kluth, P.A.

(57) ABSTRACT

The present invention provides a system and a method for discriminating supraventricular tachyarrhythmias from ventricular arrhythmias during a tachycardia episode. First cardiac signals and second cardiac signals are sampled for cardiac complexes. A first feature on the first cardiac signal and a second feature on the second cardiac signal are utilized to determine an average time difference for a plurality of normal sinus rhythm complexes. A time difference between the first feature and the second feature is then determined for each cardiac complex of a tachycardiac rhythm. The cardiac complex is characterized as a ventricular tachycardia complex if the time difference exceeds the average time difference by a predetermined amount. Otherwise, it is classified as VT if its morphology after alignment is different from that during normal sinus rhythm.

18 Claims, 13 Drawing Sheets

U.S. PATENT DOCUMENTS

| | | | | |
|---|---|---|---|---|
| 4,583,553 | A | 4/1986 | Shah et al. | 128/704 |
| 4,721,114 | A | 1/1988 | DuFault et al. | 128/696 |
| 4,838,278 | A | 6/1989 | Wang et al. | 128/697 |
| 4,924,875 | A | 5/1990 | Cahmoun | 128/696 |
| 5,000,189 | A | 3/1991 | Throne et al. | 128/702 |
| 5,014,284 | A | 5/1991 | Langer et al. | 375/30 |
| 5,014,698 | A | 5/1991 | Cohen et al. | 128/419 |
| 5,020,540 | A | 6/1991 | Chamoun | 128/696 |
| 5,107,850 | A | 4/1992 | Olive | 128/705 |
| 5,109,842 | A | 5/1992 | Adinolfi | 128/419 |
| 5,139,028 | A | 8/1992 | Steinhaus et al. | 128/697 |
| 5,156,148 | A | 10/1992 | Cohen | 128/419 |
| 5,184,615 | A | 2/1993 | Nappholz et al. | 128/419 PG |
| 5,193,550 | A | 3/1993 | Duffin | 129/697 |
| 5,215,098 | A | 6/1993 | Steinhaus et al. | 128/702 |
| 5,217,021 | A | 6/1993 | Steinhaus et al. | 128/702 |
| 5,240,009 | A | 8/1993 | Williams | 128/702 |
| 5,247,021 | A | 9/1993 | Fujisawa et al. | 525/254 |
| 5,255,186 | A | 10/1993 | Steinhaus et al. | 364/413 |
| 5,269,301 | A | 12/1993 | Cohen | 607/6 |
| 5,271,411 | A | 12/1993 | Ripley et al. | 128/702 |
| 5,273,049 | A | 12/1993 | Steinhaus et al. | 128/696 |
| 5,275,621 | A | 1/1994 | Mehra | 607/5 |
| 5,280,792 | A | 1/1994 | Leong et al. | 128/702 |
| 5,292,348 | A | 3/1994 | Saumarez et al. | 607/5 |
| 5,311,874 | A | 5/1994 | Baumann et al. | 128/705 |
| 5,312,445 | A | 5/1994 | Nappholz et al. | 607/9 |
| 5,313,953 | A | 5/1994 | Yomtov et al. | 128/696 |
| 5,330,504 | A | 7/1994 | Somerville et al. | 607/5 |
| 5,331,966 | A | 7/1994 | Bennett et al. | 128/696 |
| 5,350,406 | A | 9/1994 | Nitzsche et al. | 607/14 |
| 5,360,436 | A | 11/1994 | Alt et al. | 607/18 |
| 5,366,487 | A | 11/1994 | Adams et al. | 607/5 |
| 5,388,578 | A | 2/1995 | Yomtov et al. | 600/393 |
| 5,400,795 | A | 3/1995 | Murphy et al. | 128/702 |
| 5,411,031 | A | 5/1995 | Yomtov | 128/706 |
| 5,421,830 | A | 6/1995 | Epstein et al. | 607/30 |
| 5,447,519 | A | 9/1995 | Peterson | 607/5 |
| 5,447,524 | A | 9/1995 | Alt | 607/19 |
| 5,456,261 | A | 10/1995 | Luczyk | 128/702 |
| 5,458,623 | A | 10/1995 | Lu et al. | 607/28 |
| 5,478,807 | A | 12/1995 | Cronin et al. | 514/12 |
| 5,509,927 | A | 4/1996 | Epstein et al. | 607/32 |
| 5,520,191 | A | 5/1996 | Karlsson | 128/702 |
| 5,542,430 | A | 8/1996 | Farrugia et al. | 128/705 |
| 5,622,178 | A | 4/1997 | Gilham | 128/696 |
| 5,628,326 | A | 5/1997 | Arand et al. | 128/706 |
| 5,634,468 | A | 6/1997 | Platt et al. | 128/696 |
| 5,645,070 | A | 7/1997 | Turcott | 128/702 |
| 5,682,900 | A | 11/1997 | Arand et al. | |
| 5,683,425 | A | 11/1997 | Hauptmann | 607/9 |
| 5,687,737 | A | 11/1997 | Branham et al. | 128/710 |
| 5,704,365 | A | 1/1998 | Albrecht et al. | 128/702 |
| 5,712,801 | A | 1/1998 | Turcott | 364/550 |
| 5,713,366 | A | 2/1998 | Armstrong et al. | |
| 5,713,367 | A | 2/1998 | Arnold et al. | 128/704 |
| 5,724,985 | A | 3/1998 | Snell et al. | 128/697 |
| 5,730,142 | A | 3/1998 | Sun et al. | 128/705 |
| 5,738,105 | A | 4/1998 | Kroll | 128/708 |
| 5,755,739 | A | 5/1998 | Sun et al. | 607/14 |
| 5,759,158 | A | 6/1998 | Swanson | 600/508 |
| 5,772,604 | A | 6/1998 | Langberg et al. | 600/518 |
| 5,778,881 | A | 7/1998 | Sun et al. | 128/696 |
| 5,779,645 | A | 7/1998 | Olson et al. | 600/518 |
| 5,782,888 | A | 7/1998 | Sun et al. | 607/27 |
| 5,792,065 | A | 8/1998 | Xue et al. | 600/516 |
| 5,795,303 | A | 8/1998 | Swanson et al. | 600/509 |
| 5,797,399 | A | 8/1998 | Morris et al. | 128/705 |
| 5,797,849 | A | 8/1998 | Vesely et al. | 600/461 |
| 5,817,133 | A | 10/1998 | Houben | 607/9 |
| 5,819,007 | A | 10/1998 | Elghazzawi | 395/51 |
| 5,819,741 | A | 10/1998 | Karlsson | 128/710 |
| 5,848,972 | A | 12/1998 | Triedman et al. | 600/508 |
| 5,857,977 | A | 1/1999 | Caswell et al. | 600/518 |
| 5,858,977 | A | 1/1999 | Aukerman et al. | 514/12 |
| 5,935,082 | A | 8/1999 | Albrecht et al. | 600/515 |
| 5,954,661 | A | 9/1999 | Greenspon et al. | 600/510 |
| 6,223,078 | B1 | 4/2001 | Marcovecchio | 607/5 |
| 6,266,554 | B1 | 7/2001 | Hsu et al. | 600/515 |
| 6,275,732 | B1 | 8/2001 | Hsu et al. | 607/14 |
| 6,308,095 | B1 | 10/2001 | Hsu et al. | 600/518 |
| 6,312,388 | B1 | 11/2001 | Marcovecchio et al. | 600/508 |
| 6,434,417 | B1 | 8/2002 | Lovett | 600/509 |
| 6,449,503 | B1 | 9/2002 | Hsu | 600/518 |
| 2004/0093035 | A1 | 5/2004 | Schwartz et al. | 607/5 |

SYSTEM AND METHOD FOR ARRHYTHMIA DISCRIMINATION

CROSS REFERENCE TO RELATED APPLICATIONS

This application is a continuation of U.S. patent application Ser. No. 09/248,800, filed on Feb. 12, 1999, now issued as U.S. Pat. No. 6,308,095, the specification of which is incorporated herein by reference.

FIELD OF THE INVENTION

The subject matter relates generally to implantable medical devices and more particularly to arrhythmia discrimination with an implantable medical device.

BACKGROUND

Effective, efficient ventricular pumping action depends on proper cardiac function. Proper cardiac function, in turn, relies on the synchronized contractions of the heart at regular intervals. When normal cardiac rhythm is initiated at the sinoatrial node, the heart is said to be in sinus rhythm. However, when the heart experiences irregularities in its coordinated contraction, due to electrophysiologic disturbances caused by a disease process or from an electrical disturbance, the heart is denoted to be arrhythmic. The resulting cardiac arrhythmia impairs cardiac efficiency and can be a potential life threatening event.

Cardiac arrhythmias occurring in the atrial of the heart are called supraventricular tachyarrhythmias (SVTs). Cardiac arrhythmias occurring in the ventricular region of the heart are called ventricular tachyarrhythmias (VTs). SVTs and VTs are morphologically and physiologically distinct events. VTs take many forms, including ventricular fibrillation and ventricular tachycardia. Ventricular fibrillation is a condition denoted by extremely rapid, nonsynchronous contractions of the ventricles. This condition is fatal unless the heart is returned to sinus rhythm within a few minutes. Ventricular tachycardia are conditions denoted by a rapid heart beat, 150 to 250 beats per minute, that has its origin in some abnormal location within the ventricular myocardium. The abnormal location is typically results from damage to the ventricular myocardium from a myocardial infarction. Ventricular tachycardia can quickly degenerate into ventricular fibrillation.

SVTs also take many forms, including atrial fibrillation and atrial flutter. Both conditions are characterized by rapid uncoordinated contractions of the atria. Besides being hemodynamically inefficient, the rapid contractions of the atria can also adversely effect the ventricular rate. This occurs when the aberrant contractile impulse in the atria are transmitted to the ventricles. It is then possible for the aberrant atrial signals to induce VTs, such as a ventricular tachycardia.

Implantable cardioverter/defibrillators (ICDs) have been established as an effective treatment for patients with serious ventricular tachyarrhythmias. ICDs are able to recognize and treat tachyarrhythmias with a variety of tiered therapies. These tiered therapies range from providing antitachycardia pacing or cardioversion energy for treating ventricular tachycardia to defibrillation energy for treating ventricular fibrillation. To effectively deliver these treatments, the ICD must first identify the type of tachyrhythmia that is occurring, after which appropriate therapy is provided to the heart. A problem arises, however, when the ICD delivers therapy to treat a ventricular tachycardia that is caused and sustained by an SVT.

Delivered therapy is typically ineffective in treating the ventricular tachycardia in these instances, as the pacing and/or cardioverting electrical energy has little or no effect on the true source of the ventricular tachycardia. As a result, the ICD delivers inappropriate treatment to the patient, which besides being painful is also very disconcerting to the patient. Accurate discrimination of an SVT versus a malignant ventricular tachycardia is, therefore, an important factor in ensuring the appropriate therapy is delivered to an arrhythmic heart.

For the reasons stated above, and for other reasons stated below which will become apparent to those skilled in the art upon reading and understanding the present specification, there is a need in the art for providing a reliable system of discriminating SVT induced ventricular tachycardia from malignant ventricular tachycardia which can provide effective and reliable therapy to patients experiencing malignant ventricular tachycardia.

SUMMARY OF THE INVENTION

As explained in detail below, the present invention is directed to a system for distinguishing between the occurrence of a ventricular tachycardia (VT) and a supraventricular tachycardia (SVT) during a tachycardia episode. Upon detecting a tachycardia episode, the system determines features and/or metric values from the sensed cardiac complexes and compares them to the same general features sensed during normal sinus rhythm. Using this comparison, the system is able to distinguish the underlying cause of a tachycardia episode as either being an SVT or as a VT. Once the determination has been made, the system then provides therapy to treat the underlying cause of the tachycardia episode. In turn, this provides more effective and efficient treatment to the patient.

The present system uses information sensed from normal sinus rhythm complexes to create a template against which cardiac complexes sensed during a tachycardia episode are compared in order to classify them as either VT or SVT complexes. In one embodiment, the system uses information contained in cardiac rate signals (near-field signals) and cardiac morphology signals (far-field signals) of a transvenous lead system in distinguishing VT from SVT during a tachycardia episode. To make this distinction, the system first uses cardiac complexes sensed during normal sinus rhythm to create a normal sinus rhythm template. In one embodiment, the normal sinus rhythm template is derived from the timing differences between at a first feature point on a first signal of a cardiac complex and a second feature point on a second signal of the cardiac complex. In one embodiment, the first signal is a near-field signal and the second signal is a far-field signal.

In one embodiment, the first feature point along the first cardiac signal and the second feature point along the second cardiac signal are determined from morphological features along the cardiac signals. In one embodiment, the morphological features along the cardiac signals can be any combination of maximum deflection points of the cardiac signals, the beginning or ending of cardiac signals, and/or fiducial points along the cardiac signals. Timing differences between the first and second feature points are then determined and median or average values of the timing differences are calculated.

In addition, other metric values can be derived from the feature points, such as median or average signal amplitude values, standard deviation values from the median or average signal amplitude values, slopes and/or slew rates from the cardiac complex signals can also be used in creating the normal sinus rhythm template. Feature values from the normal sinus rhythm cardiac signals can also be recorded and stored for future comparison to cardiac signal sensed during a tachycardia episode. The stored feature values can then be used alone or in conjunction with the timing difference values and/or metric values in distinguishing VT from SVT.

In one embodiment, the system determines the timing differences and/or the other metric values from a first feature point and a second feature point taken from cardiac complexes sensed during a tachycardia episode. The system then compares the timing differences and/or cardiac metric values from the cardiac complexes and the values stored for the normal sinus rhythm template. In one embodiment, if the timing differences exceed a template time difference of the normal sinus rhythm template by a predetermined amount, the cardiac complex is characterized as a VT complex. In an additional embodiment, changes in the metric values can also be used in determining whether a cardiac complex sensed during a tachycardia episode is a VT complex or an SVT complex. When a predetermined number, or percentage, of the cardiac complexes sensed during a tachycardia episode are classified as either VT or SVT complexes, the system then responds to treat the heart.

In an additional embodiment, if the timing differences are less than the template time difference of the normal sinus rhythm template by the predetermined amount, the cardiac complex is characterized by comparing the morphology of the first signal and/or the second signal of the sensed cardiac complex to the first signal and/or the second signal of a representative normal sinus rhythm complex to classify the cardiac complex. Before a morphology comparison is made, however, a common feature in either the first signal or the second signal of both the cardiac complex and the representative normal sinus rhythm complex are aligned. The morphology of the unaligned cardiac complexes is then compared to classify the cardiac complex as either a VT complex or an SVT complex.

These and other features and advantages of the invention will become apparent from the following description of the embodiments of the invention.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments of the present system illustrated herein are described as being included in an implantable cardiac defibrillator, which may include numerous pacing modes known in the art, and an external medical device programmer. In one embodiment, the implantable cardiac defibrillator is a single chamber defibrillator. In an alternative embodiment, the implantable cardiac defibrillator is a dual chamber defibrillator. Examples of both single and dual chamber implantable cardiac defibrillators are known in the art. However, the present medical system can also be implemented in an external cardioverter/monitor system as are known in the art. Also, the present medical system can also be implemented in an implantable atrial cardioverter-defibrillator, which may include numerous pacing modes known in the art. Furthermore, although the present system is described in conjunction with an implantable cardiac defibrillator having a microprocessor based architecture, it will be understood that the implantable cardiac defibrillator (or other implanted device) may be implemented in any logic based, custom integrated circuit architecture, if desired.

Figure 1:
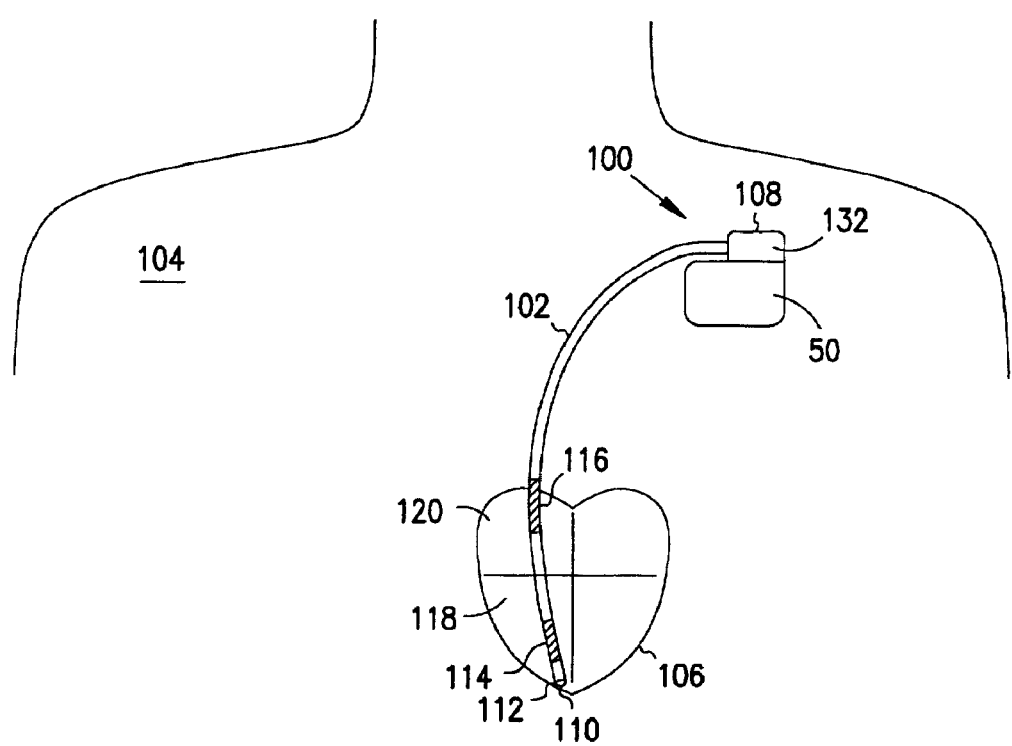
FIG. 1 is a schematic view of one embodiment of an implantable medical device with an endocardial lead implanted in a heart from which segments have been removed to show details.

Referring now to FIG. 1 of the drawings, there is shown one embodiment of a medical device system which includes an implantable cardiac defibrillator 100 electrically and physically coupled to at least one intracardiac catheter 102. In one embodiment, the intracardiac catheter 102 includes one or more pacing electrodes and one or more intracardiac defibrillation electrodes.

The intracardiac catheter 102 is implanted in a human body 104 with portions of the intracardiac catheter 102 inserted into a heart 106 to detect and analyze electric cardiac signals produced by the heart 106 and to provide electrical energy to the heart 106 under certain predetermined conditions to treat cardia arrhythmias, including ventricular fibrillation, of the heart 106.

In one embodiment, the intracardiac catheter 102 is an endocardial lead adapted to be releasably attached to the cardiac defibrillator 100. The intracardiac catheter 102 has an elongate body with a proximal end 108 and a distal end 110, and has at least one pacing electrode. In one embodiment, the intracardiac catheter 102 has a pacing electrode 112 located at, or adjacent, the distal end 110 of the intracardiac catheter 102. Additional pacing electrodes can also be included on the intracardiac catheter 102 to allow for bipolar sensing and pacing with the pacing electrode 112. In addition, other pacing and sensing electrode configurations are also possible.

In one embodiment, the intracardiac catheter 102 includes one or more defibrillation electrodes. In one embodiment, the intracardiac catheter 102 has a first defibrillation electrode 114 and a second defibrillation electrode 116, where the first defibrillation electrode 114 and the second defibrillation electrode 116 are defibrillation coil electrodes. The first defibrillation electrode 114 is spaced apart and proximal from the pacing electrode 112, and the second defibrillation electrode 116 is spaced apart and proximal from the first defibrillation electrode 114 such that when the intracardiac catheter 102 is positioned within the heart 106 the pacing electrode 112 and the first defibrillation electrode 114 reside within a right ventricle 118 of the heart 106, with the pacing electrode 112 in an apex location within the right ventricle 118, and the second defibrillation electrode 116 is positioned within the right atrium chamber 120 of the heart 106 or a major vein leading to the right atrium chamber 120 of the heart 106.

Figure 2:
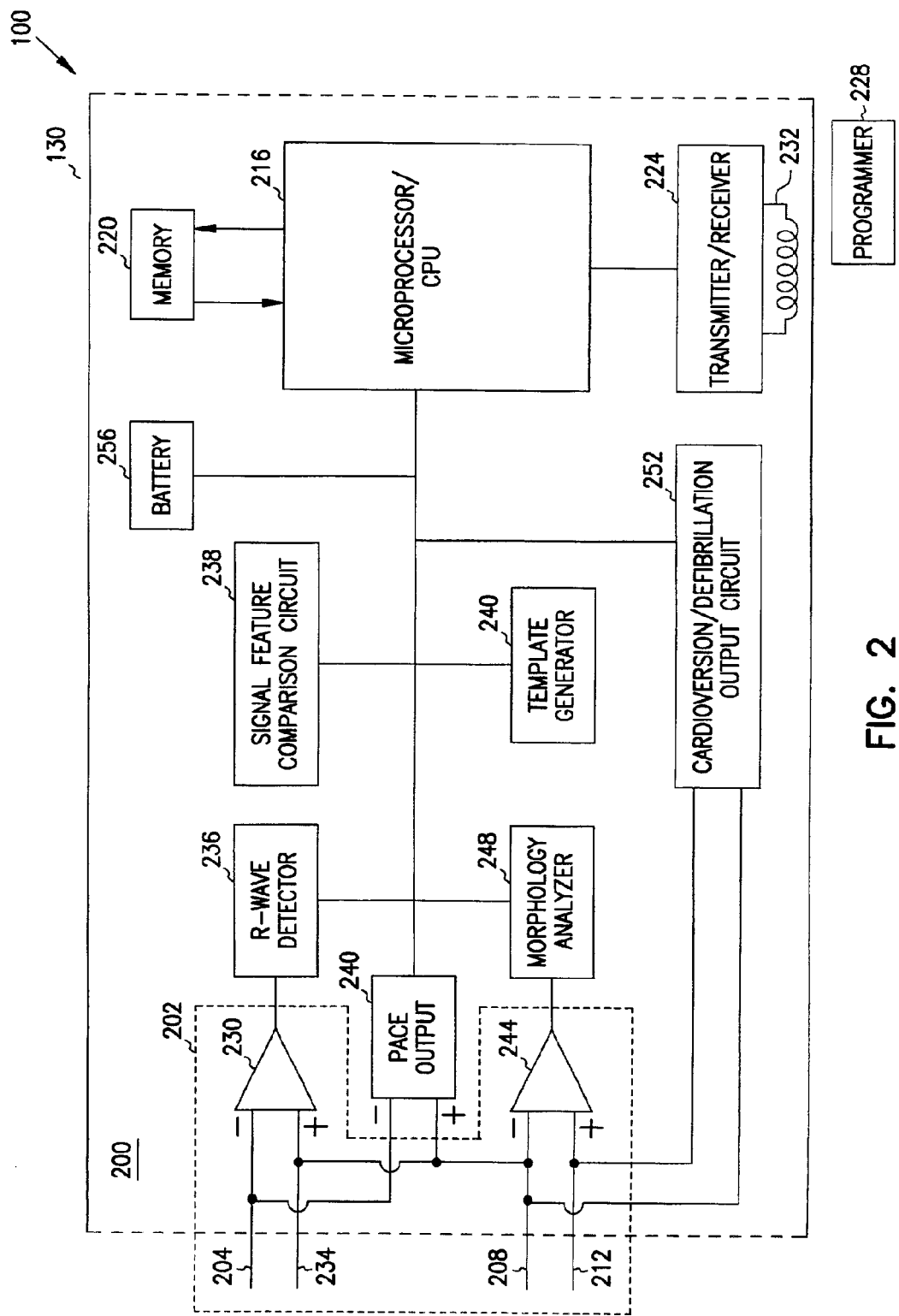
FIG. 2 is a block diagram of an implantable medical device according to one embodiment of the present system.

Referring now to FIG. 2, there is shown an embodiment of a block diagram of a cardiac defibrillator 100. The cardiac defibrillator 100 includes control system circuitry 200 for receiving cardiac signals from a heart 106 and delivering electrical energy to the heart 106. The control system circuitry 200 includes and is attached to a sensing system 202. The sensing system 202 includes terminals labeled with reference numbers 204, 208, and 212 for connection to electrodes attached to the surface of the intracardiac catheter 102. The pacing electrode 112 is electrically connected to terminal 204 and to the control system circuitry 200 through an electrically insulated conductor provided within the elongate body of the intracardiac catheter 102. The first defibrillation electrode 114 and the second defibrillation electrode 116 are connected to terminals 208 and 212, respectively, and to the control system circuitry 200 through electrically insulated conductors provided within the elongate body of the intracardiac catheter 102.

In one embodiment, the control system circuitry 200 of the cardiac defibrillator 100 is encased and hermetically sealed in a housing 130 suitable for implanting in a human body as are known in the art. A connector block 132 (FIG. 1) is additionally attached to the housing 130 of the cardiac defibrillator 100 to allow for the physical and the electrical attachment of the intracardiac catheter 102 and the electrodes to the cardiac defibrillator 100 and the encased control system circuitry 200.

In one embodiment, the control system circuitry 200 of the cardiac defibrillator 100 is a programmable microprocessor-based system, with a microprocessor 216 and a memory circuit 220, which contains parameters for various pacing, defibrillation, and sensing modes and stores data indicative of cardiac signals received by the control system circuitry 200. A transmitter circuit 224 is additionally coupled to the control system circuitry 200 and the memory circuit 220 to allow the cardiac defibrillator 100 to communicate with an programmer unit 228. In one embodiment, the transmitter circuit 224 and the programmer unit 228 use a wire loop antenna 232 and a radio frequency telemetric link, as is known in the art, to receive and transmit signals and data to and from the programmer unit 228 and the control system circuitry 200. In this manner, programming commands or instructions are transferred to the microprocessor 216 of the cardiac defibrillator 100 after implant, and stored cardiac data pertaining to sensed arrhythmic episodes within the heart 106 and subsequent therapy, or therapies, applied to correct the sensed arrhythmic event are transferred to the programmer unit 228 from the cardiac defibrillator 100.

The cardiac signals sensed through the pacing electrode 112 are near-field signals or rate signals as are known in the art. The embodiment of the cardiac defibrillator block diagram (FIG. 2) shows the pacing electrode 112 coupled to a sense amplifier 230 within the sensing system 202. In one embodiment, the housing 130 of the cardiac defibrillator 100 is coupled to the sense amplified 230 at 234 to allow for unipolar cardiac rate sensing between the pacing electrode 112 and the housing 130 of the cardiac defibrillator 100. In an alternative embodiment, the cardiac rate signal is sensed using pacing electrode 112 and the first defibrillation electrode 114.

The output of the sense amplifier 230 is shown connected to an R-wave detector 236. In one embodiment, the input to the R-wave detector 236 are the rate signals. The R-wave detector 236 serves to sense and amplify the electrical activity of the heart (R-waves), and apply signals indicative thereof to a signal feature comparison circuit 238. The signal feature comparison circuit 238 is coupled to the microprocessor 216. Among other things, microprocessor 216 responds to signals from the R-wave detector 236 by providing pacing signals to a pace output circuit 240, as needed according to the programmed pacing mode. Pace output circuit 240 provides output pacing signals to terminals 204 and 234, which connect to the pacing electrode 112 and the housing 130 of the cardiac defibrillator 100, for cardiac pacing.

Cardiac signals sensed through the first defibrillation electrode 114 and the second defibrillation electrode 116 are far-field signals or morphology signals as are known in the art. The first defibrillation electrode 114 and the second defibrillation electrode 116 are coupled to a sense amplifier 244, which is used to sense far-field signals from the heart. In an alternative embodiment, far-field signals are sensed between the first defibrillation electrode 114, the second defibrillation electrode 116 and the housing 130. The output of the sense amplifier 244 is coupled to a morphology analyzer circuit 248. In one embodiment, the morphology analyzer circuit locates features along cardiac signals sensed by the control system circuitry 200.

In one embodiment, the sense amplifier 244 amplifies cardiac electrical activation sequences (such as the QRS-waves of the cardiac cycle) sensed in the ventricular region of the heart 106. After the signals have passed through the morphology analyzer circuit 248, the signals are received by a signal feature comparison circuit 238 which is coupled to the morphology analyzer circuit 248. In one embodiment, the signal feature comparison circuit 238 determines a time difference between the features tachycardia complexes sensed by the sensing system 202 and compares the time differences to a template time difference determined from the time difference between features for a plurality of cardiac complexes sensed during normal sinus rhythm.

In one embodiment, the morphology analyzer circuit 248 includes an analog filter for filtering cardiac signal noise sensed by the electrodes. The cardiac signals are then bandlimited before arriving at an analog-to-digital filter. The cardiac signals are then A/D converted into a digital signal and subsequently received by the signal feature comparison circuit 238 and then by the microprocessor 216. In an alternative embodiment, the cardiac signals are filtered through an analog peak detector to extract the maximum and minimum cardiac signal values for each sensed cardiac interval before being received by the signal feature comparison circuit 238 and then by the microprocessor 216.

The signal feature comparison circuit 238 uses information contained in the far-field and the near-field sensing channels of a transvenous lead system in discriminating ventricular tachycardias (VT) from non-malignant supraventricular tachycardias (SVT) during a tachycardia episode. In one embodiment, the signal feature comparison circuit 238 discriminates VT from SVT by comparing cardiac complexes sensed during a tachycardia episode to a normal sinus rhythm template. In another embodiment, the normal sinus rhythm template is generated on a patient-by-patient basis with a template generator 240 from sensed normal sinus rhythm complexes. The normal sinus rhythm template contains information related to specific characteristics of a patient's cardiac complexes sensed with their implantable medical device during normal sinus rhythm. By sensing cardiac complexes using at least two different types of sensing configurations (e.g. sensing near-field and far field signals for each sensed cardiac complex) the differences observed between the sensed cardiac complexes and the normal sinus template acquired during normal sinus rhythm can be used to determine the origin of the tachycardia episode.

Upon determining the origin of the sensed tachycardia episode, the microprocessor 216 responds by providing signals to cardioversion/defibrillation output circuitry 252 to deliver either cardioversion or defibrillation electrical energy to the heart 106 depending upon whether the tachycardia episode was determined to be a VT or an SVT. Power to the cardiac defibrillator 100 is supplied by an electrochemical battery 256 that is housed within the cardiac defibrillator 100.

In addition to the intracardiac catheter 102, it is possible to add additional electrodes, catheters and the accompanying required circuitry to the medical device system. For example, the cardiac defibrillator 100 can be equipped with electrodes on the surface of the housing 130 to sense surface like cardiac signals. In addition, the medical device system can further include an additional intracardiac catheter implanted in the supraventricular region of the heart. The additional intracardiac catheter includes at least one pacing electrode from which rate signals, or near field signals, from the atria are sensed and pacing pulses are delivered to pace the atrial chamber of the patient's heart. In an additional embodiment, the additional intracardiac catheter is implanted through the coronary sinus vein and down the great cardiac vein to position an electrode, such as a pacing electrode, adjacent to the left ventricular chamber of the heart. In an alternative embodiment, the intracardiac catheter 102 is implanted the supraventricular region of the heart for sensing cardiac signals from the patient's atrial regions. In one embodiment, a pacing electrode at or adjacent the distal end of the intracardiac catheter is implanted in the coronary sinus vein to allow for rate signals to be sensed from the left atrium. In addition, far-field signals, or morphology signals, are sensed from the supraventricular region of the heart through the first defibrillation electrode and the second defibrillation electrode. In addition to implanting the intracardiac catheter 102 in the supraventricular region of the heart, an additional atrial catheter can be implanted into the supraventricular region of the heart to allow for additional rate signals, or near-field signals, to be sensed along with the rate signals and morphology signals sensed with the intracardiac catheter 102. Other intracardiac catheter arrangements and configurations known in the art are also possible and considered to be within the scope of the present system.

With respect to the present system, prompt diagnosis and treatment of a tachycardia episode is important to a patient's health, as an untreated tachycardia episode has the potential, if the episode is a ventricular tachycardia, to degenerate into a ventricular fibrillation. Therefore, accurately discriminating VT from SVT during a tachycardia episode in a quick and effective manner is critical in delivering the most appropriate and effective treatment to the patient. As was previously mentioned, determining the origin of a detected tachycardia episode is an important aspect of diagnosing and treating the patient's condition. Implantable cardioverter defibrillators frequently deliver inappropriate ventricular therapy to patients afflicted with an SVT. These inappropriate therapies are usually delivered due to the device's inability to reliably discriminate SVT from malignant ventricular tachycardias (VT). Therefore, when the tachycardia episode is a VT, anti-tachycardia therapy delivered to the ventricles of the heart can be effectively directed at the source or origin of the problem. In contrast, if the detected tachycardia episode is an SVT, delivering anti-tachycardia therapy to the ventricles of the heart will be ineffective in treating the underlying cause of the tachycardia episode.

One aspect of the present system is to address the problem of differentiating, or discriminating, whether a detected tachycardia episode is the result of an SVT or an a VT episode in the heart. In one embodiment, the present system utilizes the medical device system to differentiate, or distinguish, between SVT and VT episodes when a tachycardia episode is detected.

Figure 3:
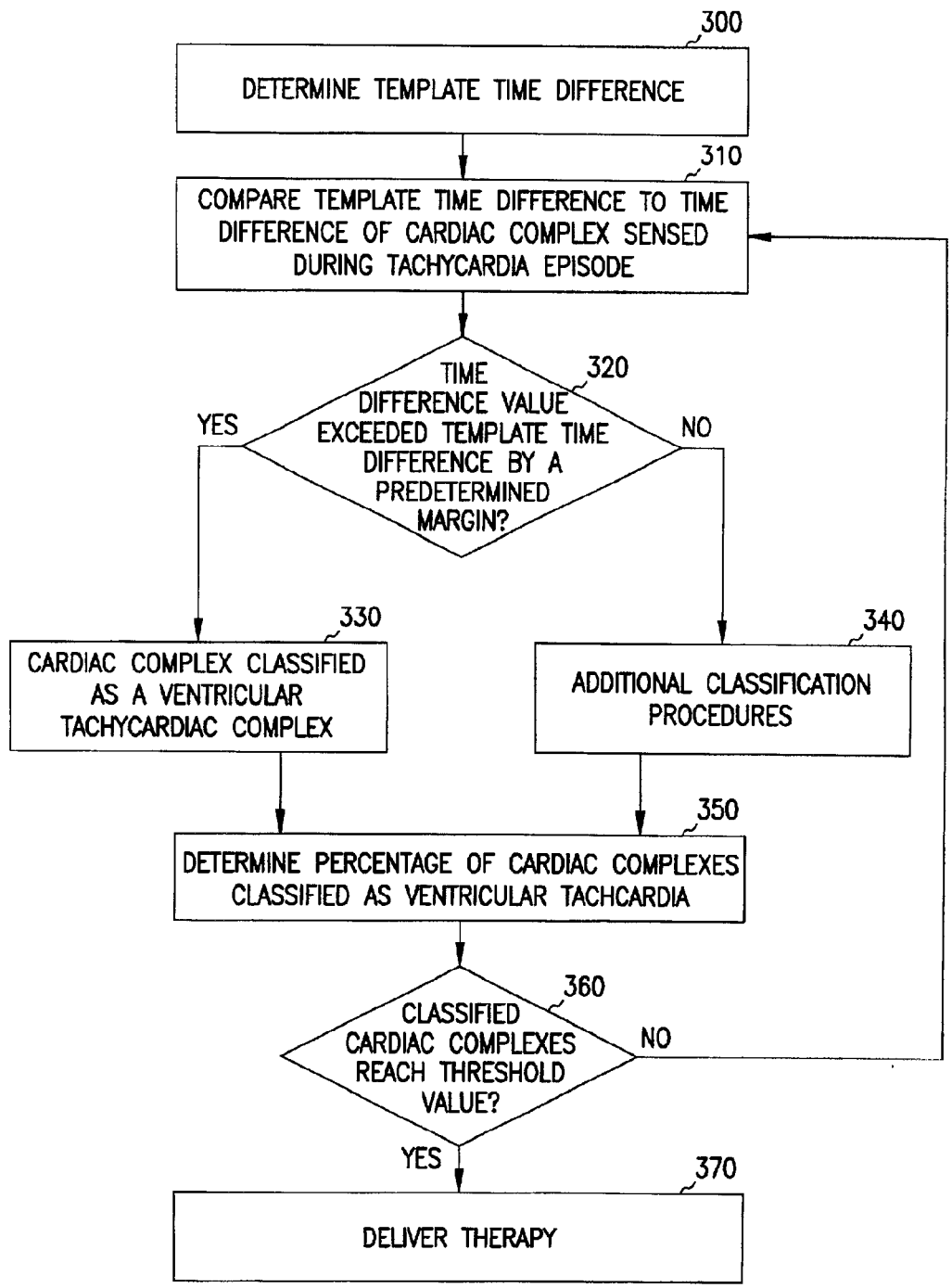
FIG. 3 is a flow diagram illustrating one embodiment of the present system.

Referring to FIG. 3, there is shown one embodiment of the present system for distinguishing between SVT and VT episodes. In one embodiment, the present system differentiates between VT and SVT during a tachycardia episode by performing a cross channel analysis of the sensed cardiac complexes. The cross channel analysis exploits the difference in activation sequence between normally conducted activation sequences and those resulting from a ventricular tachycardia. In one embodiment, the cross channel analysis determines timing differences between predetermined features on cardiac complexes sensed by at least a near-field channel and a far-field channel. The timing differences are then used in determining the origin of the tachycardia episode.

At 300, a plurality of cardiac complexes are sensed during normal sinus rhythm. In one embodiment, a near-field channel and a far-field channel are used to sense the cardiac complexes during the normal sinus rhythm. In one embodiment, the near-field signal (rate signal) is sensed from the pacing electrode 112 to the first defibrillation electrode 114, both of which are located in the right ventricle. The far-field signal (the morphology channel) is sensed between the first defibrillation electrode 114, the second defibrillation electrode 116 and the housing 130 of the implantable pulse generator. As a result, each cardiac complex sensed during the normal sinus rhythm has associated with signals sensed from two different cardiac channels (i.e., a near-field and a far-field signal). This necessarily means that the differentiation, or determination, of the tachycardia episode as being either a VT or SVT is based on characteristics of cardiac complexes sensed in, or across, at least two different areas of the heart. In addition to using near-field and far-field signals sensed from the right ventricles and/or atria of the heart, it is also possible to use any combination of these types of signals with cardiac signals sensed from the left side of the heart.

As the cardiac complexes are sensed, predetermined features are located along each of the near-field and a far-field signals for the cardiac complexes. In one embodiment, the template time difference is calculated from timing differences for a plurality of cardiac electrical activation sequences (e.g., QRS-cardiac complexes) sensed during normal sinus rhythm. In one embodiment, the template time difference is the median time difference between the relative timing of features on the cardiac signal sensed in each of a plurality of sensing channels during a patient's normal sinus rhythm. In an alternative embodiment, the template time difference is the average time difference between the relative timing of features on the cardiac signal sensed in each of a plurality of sensing channels during a patient's normal sinus rhythm. Therefore, in one embodiment, a timing difference is determined between the predetermined feature, or features, on the near-field signal and the predetermined feature, or features, on the far-field signal for each sensed cardiac complex. In one embodiment, from the plurality of cardiac complexes, a template time difference is determined from the patient's cardiac complexes sensed during normal sinus rhythm. In addition to sensing cardiac signals during a patient's normal sinus rhythm, a pre-processing step can be added to the system to exclude premature ventricular contraction signals from being included in the determination of the template time difference value. Once the template time difference is calculated it is stored in the medical device system.

At 310, the template time difference is compared to a time difference calculated from the corresponding features on a cardiac complex sensed during a tachycardia episode. In one embodiment, the time difference is calculated using the same method used to acquire and compute the time differences during normal sinus rhythm. Based on the comparison, a decision is made at 320 whether the time difference value exceeds the template time difference value by a predetermined margin. In one embodiment, the system proceeds to 330 when the time difference exceeds the template time difference by the predetermined margin. The cardiac complex is then classified as a VT complex. However, if the time difference does not exceed the template time difference by the predetermined margin, the system proceeds to 340. At 340, the system utilizes additional procedures to classify the cardiac complex as either VT complex or non-VT complex. If the additional classification procedures determine the cardiac complex to be a non-VT complex and/or an SVT complex, the system passes the information to 350 and then returns to 310 to continue to sense and analyze cardiac complexes. Alternatively, if the additional classification procedure classifies the cardiac complex as a VT complex the information is passed to 350 where the percentage of cardiac complexes classified as ventricular tachycardias is determined.

As each sensed cardiac complex is classified, percentage values for cardiac complexes classified as VT complexes and SVT complexes are calculated at 350. At 360, a decision is made whether the percentage of cardiac complexes classified as either VT or SVT has reached a predetermined percentage threshold. If the percentage of cardiac complexes has not reached the threshold value, the system returns to 310 to analyze the next cardiac complex. If the percentage of cardiac complexes has reached the threshold value, the system proceeds to 370, where the tachycardia episode is declared as either VT or SVT and the appropriate therapy is delivered to the patient to terminate the convert the heart to normal sinus rhythm.

As mentioned, values derived from characteristics of cardiac complexes signals sensed during a tachycardia episode are compared to values derived from cardiac complex characteristics sensed during normal sinus rhythm. In one embodiment, the values compared are timing differences between morphological characteristics, or characteristic values, on at least two different cardiac sensing channels (e.g., far-field signals and near-field signals) for cardiac complexes sensed during normal sinus rhythm and for cardiac complexes sensed during a tachycardia episode where the origin of the tachycardia is unknown.

In one embodiment, the values for timing differences between the morphological characteristics from the different cardiac sensing channels are calculated, stored and subsequently used by comparing them to the timing differences calculated from the corresponding morphological characteristics, or characteristic values, of cardiac complexes sensed during a tachycardia episode. Based on the comparison between the normal sinus rhythm characteristic value (e.g., the timing differences between the morphological characteristics) and the characteristic value for the cardiac complex sensed during the tachycardia episode, the cardiac complex is classified as either being a VT complex or an SVT complex. Finally, it is possible to use a combination of timing differences between the morphological features on cardiac complex signals and morphological characteristics of cardiac complexes sensed using at least two different types of cardiac sensing channels, such as far-field and near-field sensing.

Figure 4A:
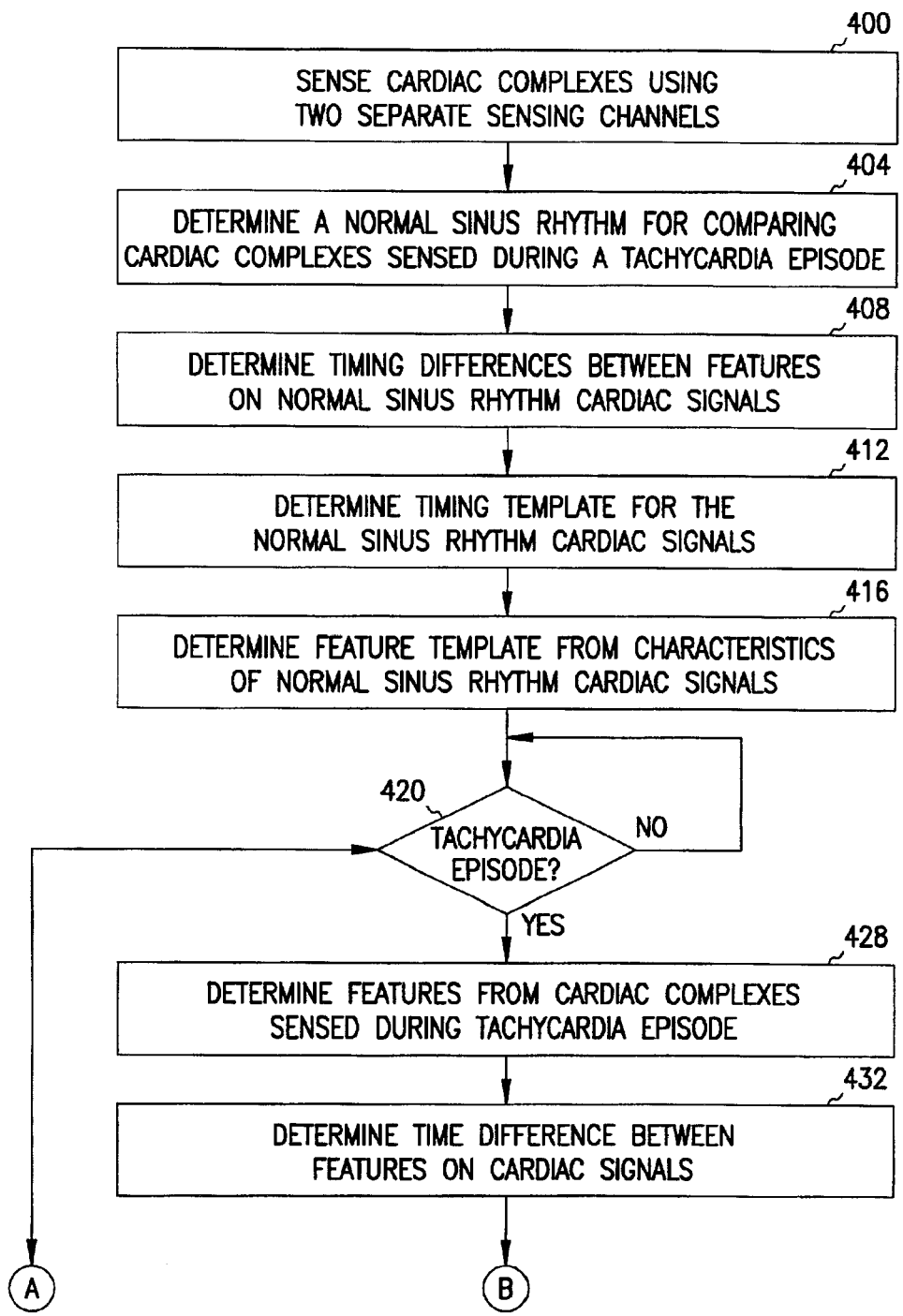
FIGS. 4A and 4B are a flow diagram illustrating one embodiment of the present system.
Figure 4B:
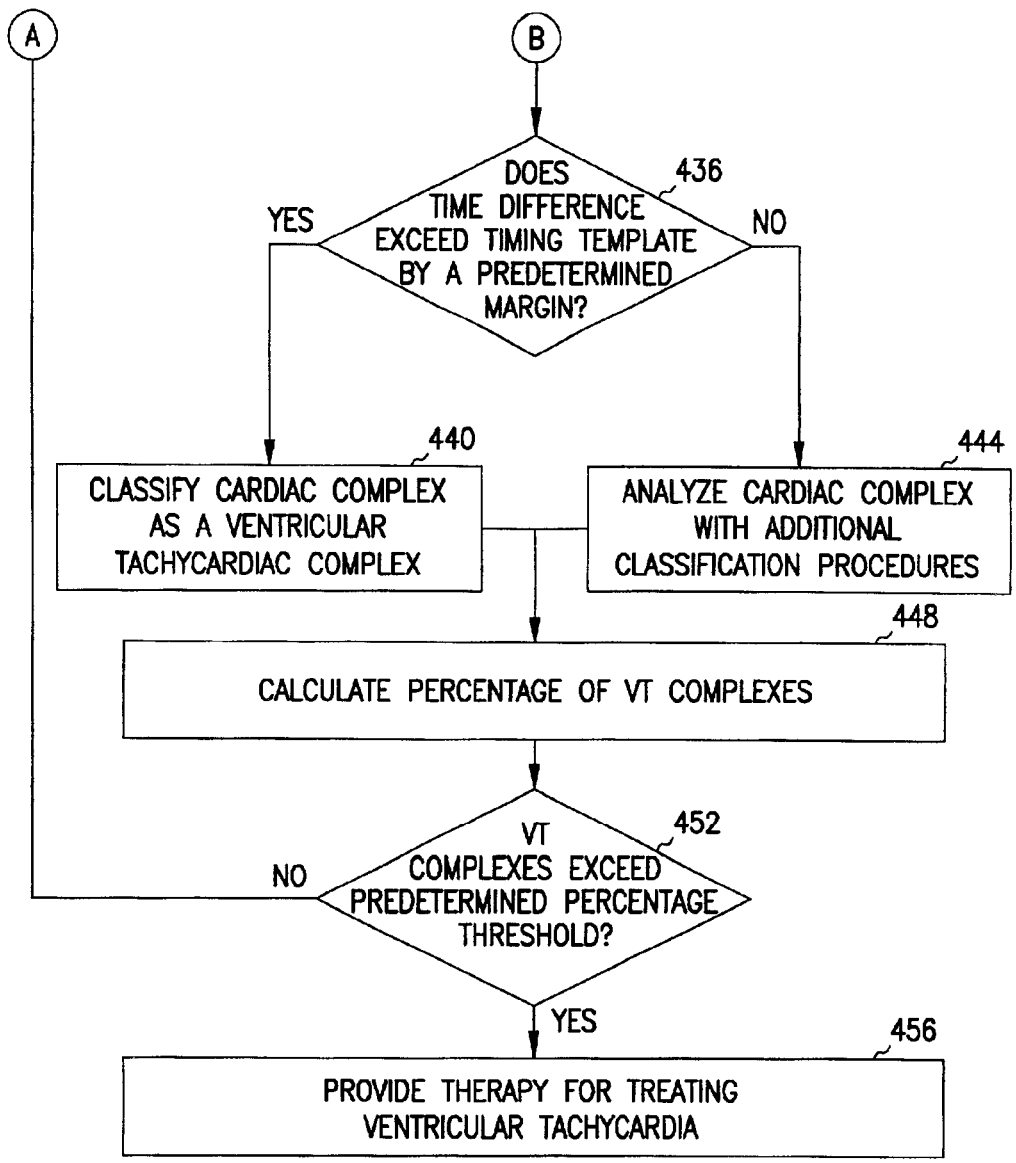

Referring now to FIGS. 4A and 4B, there is shown an alternative embodiment of the present system. At step 400, a medical device system, such as the cardiac defibrillator 100, senses cardiac signals during normal sinus rhythm using two or more simultaneous sensing channels. In one embodiment, the two or more simultaneous sensing channels include both a far-field channel and a near field channel. In providing two or more simultaneous sensing channels, cardiac complexes of the heart are being sensed from at least two different cardiac locations. So, sensed cardiac complexes include at least a first signal representative of electrical activity of the heart sensed at a first cardiac region, and a second signal representative of electrical activity of the heart is sensed at a second cardiac region. In the present embodiment, the sensed cardiac signals include cardiac electrical activation sequences (e.g., QRS-cardiac complexes) representative of a cardiac cycle.

In one embodiment, the first cardiac region and the second cardiac region are in or adjacent ventricular regions of the heart. This allows for ventricular activity to be sensed in a plurality of locations by the medical device system. In an alternative embodiment, the first cardiac region and the second cardiac region are both in a supraventricular region of the heart. In this embodiment, the medical device system senses cardiac complexes indicative of atrial activity. In an alternative embodiment, both an atrial region of the heart and a ventricular region of the heart are used as the first cardiac region and the second cardiac region. For example, one of the first cardiac region or the second cardiac region is a ventricular region of the heart, such as the right ventricle, while the remaining cardiac region is an area of the patient's heart sensed across, or in, both the ventricular and atrial regions of the heart.

The medical device system can also be configured to sense any combination of cardiac near-field signals (rate signal) and/or far-field signals (morphology signal). This will depend upon the electrode system employed to sense each cardiac region in the heart. In one embodiment, two or more cardiac near-field signals are sensed from two or more cardiac regions in the heart. In an alternative embodiment, two or more cardiac far-field signals are sensed from two or more cardiac regions in the heart. In an additional embodiment, at least one of a cardiac far-field signal and at least one of a cardiac near-field signal are sensed from two or more cardiac regions in the heart. Additionally, cardiac signals can be sensed by electrodes positioned on the housing of an implantable system.

At 404, a normal sinus rhythm template, or model, is computed from cardiac complexes sensed during normal sinus rhythm at 400. In one embodiment, the purpose of the normal sinus rhythm template is to record the feature values corresponding to a normal sinus rhythm. After the normal sinus rhythm template is calculated, it is stored and subsequently used during a tachycardia episode to determine the origin of the tachycardia episode. In one embodiment, the template is determined from timing differences between features on the cardiac complexes sensed during normal sinus rhythm. In an alternative embodiment, the template is determined from characteristics of the sensed cardiac signals sensed during normal sinus rhythm.

In addition, the template can be updated, either manually or automatically, to reflect changes in a patient's implantable medical device. For example, timing differences for the template could change due to the type of drug or dosage of drugs being delivered to the patient and the cardiac disease state of the patient. Therefore, the system is able to recompute the normal sinus rhythm timing template at regular intervals based either on the physician's judgement or on the implantable medical devices assessment of the template. Additionally, a safe-check algorithm is used in conjunction with any automatic updating procedure to ensure that only normal sinus rhythm complexes are used in updating the template.

In one embodiment, the template is derived from timing differences between features on the cardiac signals. In deriving the timing difference, the medical device system first determines the occurrence of a first feature on the first cardiac signal and a second feature on the second cardiac signal. In one embodiment, the morphology analyzer circuit 248 is used to locate features along the cardiac signals received by the cardiac defibrillator 100. In one embodiment, the first feature and the second feature are based on a selection criteria. The selection criteria is used to identify a first portion and a second portion of the cardiac complex which is repeatably identifiable in subsequent cardiac complexes. In one embodiment, the selection criterion includes a point at the beginning of the sensed cardiac signal. In one embodiment, the beginning of the QRS-cardiac complex is determined by sensing a predetermined deviation of the first signal from a baseline signal of the first signal and of the second signal from a baseline signal of the second signal.

Alternatively, the selection criterion is a maximum deflection point of the cardiac signal, such as a maximum absolute value (i.e., largest maximum or minimum value) point along either the first cardiac signal or the second cardiac signal. In an additional embodiment, the selection criterion is a point at the end of the sensed cardiac signal. In one embodiment, the end of a QRS-cardiac complex is determined by sensing the point at which the first signal returns to a baseline signal of the first signal within a predetermined time window and the point at which the second signal returns to a baseline signal of the second signal for the predetermined time window. The selection criterion can also be the fiducial point along the sensed cardiac signal, where the fiducial point is the point along the cardiac signal with the largest first derivative of the electrogram signal (i.e., the point of largest slope along the sensed QRS-cardiac complex signal) Alternatively, the selection criterion is any repeatably identifiable feature along sensed cardiac signals.

In an alternative embodiment, the template is determined from characteristics of the sensed cardiac signals sensed during normal sinus rhythm. In one embodiment, the characteristic of the sensed cardiac signal is the slope of a predetermined portion of the cardiac signal. In an additional embodiment, the characteristic used to create the template is the amplitude of a maximum deflection point (point along the sensed signal having the maximum absolute value) of the cardiac signal, such as a maximum or minimum point along either the first cardiac signal or the second cardiac signal. In an alternative embodiment, the characteristic is the slew rate of the cardiac signals sensed during normal sinus rhythm.

Figure 5:
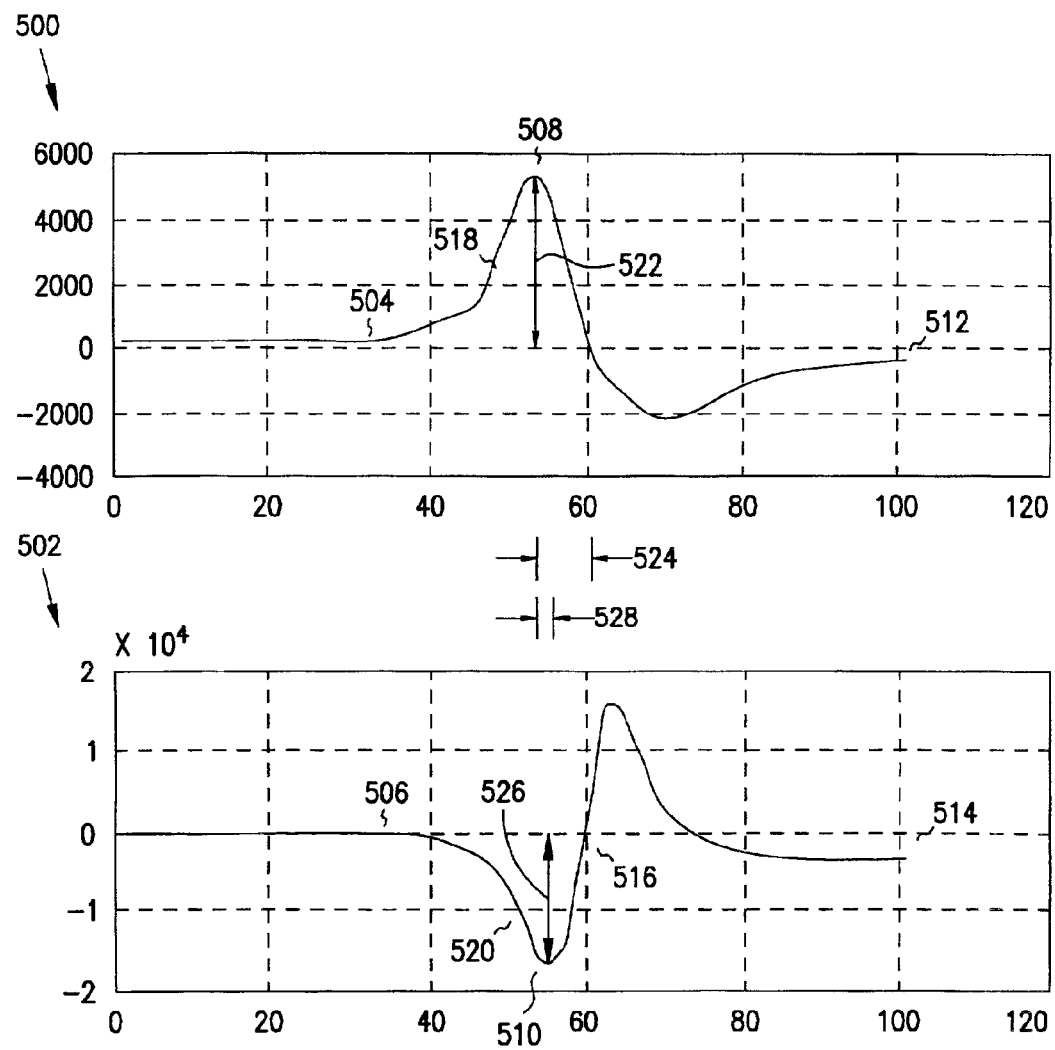
FIG. 5 is an example of a far-field signal and a near-field signal from a normal rhythm complex.

FIG. 5 shows examples of the possible selection criteria useful with the present system. FIG. 5 shows examples of a first cardiac signal 500 and a second cardiac signal 502 of a cardiac electrical activation sequence (e.g., a QRS-cardiac complex). In the present embodiment, the first cardiac signal 500 and the second cardiac signal 502 were recorded during normal sinus rhythm. The first cardiac signal 500 is an example of a far-field cardiac signal, and the second cardiac signal 502 is an example of a near-field cardiac signal. As previously mentioned, a variety of selection criterion can be selected and use to identify features along the cardiac signals that are repeatably identifiable. For example, the selection criterion used is determining a point at the beginning of the QRS-cardiac complex. In one embodiment, this point is shown approximately at 504 for the first cardiac signal 500 and at 506 for the second cardiac signal 502. In one embodiment, the beginning of the QRS-cardiac complex is denoted by the deflection in the first signal and the second signal which is caused by an intrinsic contraction of the heart.

In an alternative embodiment, the selection criterion is a maximum absolute value (i.e., largest maximum or minimum value) point of the QRS-cardiac complex. FIG. 5 shows the maximum deflection point (largest absolute peak) of the cardiac signal at approximately 508 for the first cardiac signal 500 and 510 for the second cardiac signal 502. In one embodiment, the maximum point of the QRS-cardiac complex is indicated by a point in the first signal and the second signal having approximately the largest deflection from a baseline signal. In one embodiment, the baseline signal is the approximate value of the signal between the occurrence of QRS-cardiac complexes. The location and size of the maximum point of the QRS-cardiac complex will depend upon the location and type electrodes used to sense the heart. In one embodiment, when the medical device system is the cardiac defibrillator 100 of FIG. 1, the maximum point in the first signal and the second signal is caused by the occurrence of the ventricular R-wave.

In an additional embodiment, the selection criterion is determining a point at the end of the cardiac electrical activation sequence (the QRS-cardiac complex). In one embodiment, the end of the QRS-cardiac complex is denoted by the first signal and the second signal returning to a baseline value after the occurrence of an intrinsic contraction of the heart. FIG. 5 shows the point at the end of the sensed cardiac signal approximately at 512 for the first cardiac signal 500 and at 514 for the second cardiac signal 502. In a further embodiment, the selection criterion is a fiducial point, which is shown at approximately 516 on the second cardiac signal 502.

In an alternative embodiment, characteristics of the cardiac signal are used in creating the template. In one embodiment, the slope of the cardiac signal is used as the selection criteria, where the slope is taken along the first major inflection of the cardiac signal which is shown approximately at 518 for the first cardiac signal 500 and at 520 for the second cardiac signal 502. In an additional embodiment, the amplitude of the amplitude of the maximum deflection point is used to create the template. One embodiment of the amplitude of a maximum deflection point is shown at 522 for the first cardiac signal 500 and at 526 for the second cardiac signal 502. In an alternative embodiment, the characteristic used to determined the template is the slew rate of the cardiac signals sensed during normal sinus rhythm.

In an additional embodiment, when two or more peaks along a cardiac signal have approximately the same maximum absolute value, the system is programmed to make a choice between the two portions of the signal to use as the maximum deflection point. In one embodiment, the system is programmed to select the maximum deflection point that is encountered first. In an alterative embodiment, the system is programmed to select the maximum deflection point that is encountered second. Subsequent maximum deflection points on signals sensed during either normal sinus rhythm or during a tachycardia episode are then determined from the same relative signal programmed into the system.

Referring again to FIGS. 4A and 4B, at step 408 the time difference between features on the cardiac complexes are determined for the cardiac complexes sensed during normal sinus rhythm. Because the cardiac complexes are being sensed at different cardiac locations (e.g., the first cardiac location and the second cardiac location), there is an inherent difference in the time that the cardiac complexes will be sensed. As a result, the timing difference can be taken between corresponding features on cardiac complexes. For example, in FIG. 5 there is a time difference 528 between 508 and 510 when the selection criterion is a maximum deflection point of the cardiac complex. In an additional example, there is a time difference 524 between the largest absolute peak 508 in the first cardiac signal 500 and the fiducial point 516 in the second cardiac signal 502.

In addition to determining time differences between corresponding features on cardiac complex, it is also possible to determine timing differences between different combination of features on the cardiac complexes. When more than two cardiac complexes are sensed, time differences between the selected features for any or all of the combinations of cardiac complexes may be use in creating the template for the normal sinus rhythm.

At step 412, the timing template for the normal sinus rhythm cardiac complexes is determined. In one embodiment, the timing template is a median value of the timing differences between the features on a plurality of cardiac complexes sensed during normal sinus rhythm. In an alternative embodiment, the timing template is an average value of the timing differences between the features on a plurality of cardiac complexes sensed during normal sinus rhythm. In one embodiment, the medical device system senses complexes during normal sinus rhythm and determines a template time difference between a first feature on the first signal and a second feature on the second signal for a plurality of QRS-cardiac complexes. In one embodiment, the timing template is computed from five (5) or more cardiac complexes sensed during normal sinus rhythm. In one embodiment, the five (5) or more cardiac complexes are cardiac complexes signals consecutively, or sequentially, sensed during normal sinus rhythm. In one embodiment, if the variability in the template time difference calculated during normal sinus rhythm is greater than or equal to approximately 10 milliseconds, the template time difference value is redetermined. Alternatively, the variability in the template time difference at which the template time difference will be redetermined is a predetermined value in the range of 0 to 40 milliseconds, where 10 milliseconds is an acceptable value.

In addition to calculating the timing template, a feature template is also computed at 416. The feature template is derived from the characteristics of the sensed cardiac complexes. In one embodiment, the feature template is a median signal amplitude of one or more features on the cardiac complexes sensed during normal sinus rhythm. In one embodiment, the medical device system senses complexes during normal sinus rhythm and determines a median signal amplitude for the first feature and the second feature from a plurality of normal sinus rhythm complexes. In one embodiment, the median signal amplitude for the first feature is determined relative a baseline signal of the first signal and the median signal amplitude for the second feature is determined relative a baseline signal of the second signal. In one embodiment, median signal amplitudes are computed from five (5) or more cardiac complexes sensed during normal sinus rhythm. In one embodiment, the five (5) or more cardiac complexes are cardiac complexes signals sequentially sensed during normal sinus rhythm. In one embodiment, if the variability in the median signal amplitude calculated during normal sinus rhythm is greater than or equal to approximately 20 percent, the median signal amplitude is redetermined.

When the medical device system encounters a tachycardia episode, a signal amplitude of the first feature point and the second feature point for a sensed cardiac complex is determined. In one embodiment, the signal amplitude for the first feature and the second feature are calculated relative the baseline signal of the first signal and the second signal respectively. The signal amplitude of the first feature point and the second feature point are then compared to the corresponding median signal amplitude of the first feature point and the second feature point, and if the signal amplitude of at least one of the first feature and the second feature exceeds the corresponding median signal amplitude of the first feature and the second feature by a predetermined amount, the cardiac complex is characterized as a VT complex.

Other features of the first signal and the second signal are also useful in determining whether a cardiac complex is a VT complex. In one embodiment, the medical device system senses the first signal representative of electrical activity at a first cardiac region, where the first signal includes a QRS-complex representative of a cardiac cycle. The medical device system also senses the second signal representative of electrical activity at a second cardiac region, where the second signal including the QRS-complex as sensed in the second cardiac region. Initially, a representative slope value for both the first signal and the second signal is determined from a plurality of normal sinus rhythm complexes. In one embodiment, the representative slope value is a median slope value derived from the plurality of normal sinus rhythm complexes.

During a tachycardia episode, the medical device system senses cardiac complexes (e.g., QRS-cardiac complexes) and determines a first slope for the first signal and a second slope for the second signal. In one embodiment, both the first signal and the second signal are maximum slopes (the fiducial point) for both the first signal and the second signal. The medical device system then compares the maximum slope of the first signal and the second signal of the QRS-cardiac complex to the corresponding representative slope for the first signal and the second signal. Based on this comparison, if the slope of at least one of the first signal and/or the second signal deviates from the corresponding representative slope for the first signal and the second signal by a predetermined amount, the cardiac complex is characterized as a ventricular tachycardia complex. In one embodiment, the predetermined amount is based on the percent deviation of the first signal and/or the second signal from the corresponding representative slope, where the predetermined amount is greater than or equal to 20% deviation.

Referring again to FIGS. 4A and 4B, at 420 cardiac complexes are sensed to determined the onset of a tachycardia episode. If no tachycardia episode is sensed, the system continues to sense cardiac signals and analyzes them for the occurrence of a tachycardia episode. In one embodiment, the occurrence of a tachycardia episode is based on the cardiac rate, where a tachycardia episode is declared when the cardiac rate exceeds a predetermined threshold. In one embodiment, the predetermined threshold is a cardiac rate of between 150 and 180 beats per minute. Other systems of determining the occurrence of a tachycardia episode are known and are considered to be within the scope of the present system.

When a tachycardia episode is detected the system then proceeds to 428. At 428, cardiac complexes from the tachycardia episode are sensed and features from the sensed cardiac complexes are determined. The features determined on the cardiac complexes of the tachycardia episode are the corresponding features that were detected in the cardiac complexes during normal sinus rhythm. In other words, the features and characteristics that were used in determining the timing template and the feature template during normal sinus rhythm are the features and characteristics that are extracted from the cardiac signals sensed during the ventricular tachycardia episode.

In one embodiment, the determination of whether a QRS-cardiac complex of a tachycardia episode is a VT complex or a SVT complex is based on a comparison of time differences between features on the sensed normal sinus rhythm and tachycardia episode complexes. When the medical device encounters a tachycardia episode, a time difference for each cardiac electrical activation sequence sensed during the tachycardia episode is determined. In one embodiment, the medical device system determines the time difference between the occurrence of the first feature on the first signal and the second feature on the second signal of the QRS-cardiac complex at 432. The time difference of the QRS-cardiac complex is then compared to the template time difference calculated for normal sinus rhythm at 436. Based on the comparison, if the time difference of the cardiac complex exceeds the template time difference by a predetermined margin, the cardiac complex is characterized as a ventricular tachycardia complex at 440.

In one embodiment, a ventricular tachycardiac complex is a cardiac complex that is characteristic of the occurrence of the ventricular tachycardia episode. In other words, the ventricular tachycardiac complex is a cardiac complex that makes up the occurrence of the ventricular tachycardiac episode. In one embodiment, the predetermined margin is a value which is programmable in the range of 0 to 40 milliseconds, where 10 milliseconds is an appropriate value. The time programmed for the predetermined margin will depend upon the resolution of the measuring device used within the implantable medical device.

In one embodiment, the predetermined margin programmed into the implantable medical device will depend on the cardiac signal features used in determining the timing differences. For example, when timing differences being used are between the largest peak in the morphology channel signal (far-field channel) and the fiducial point along the rate channel signal, the predetermined margin is approximately plus or minus 10 milliseconds. In other words, if the timing difference for the tachycardia complex and the template complex differs by more than 10 milliseconds, the complex is classified as a VT complex. In this embodiment, the predetermined margin, or threshold, of 10 milliseconds is sufficient for most patients, however, the value may need to be customized for some patients.

Figure 6:
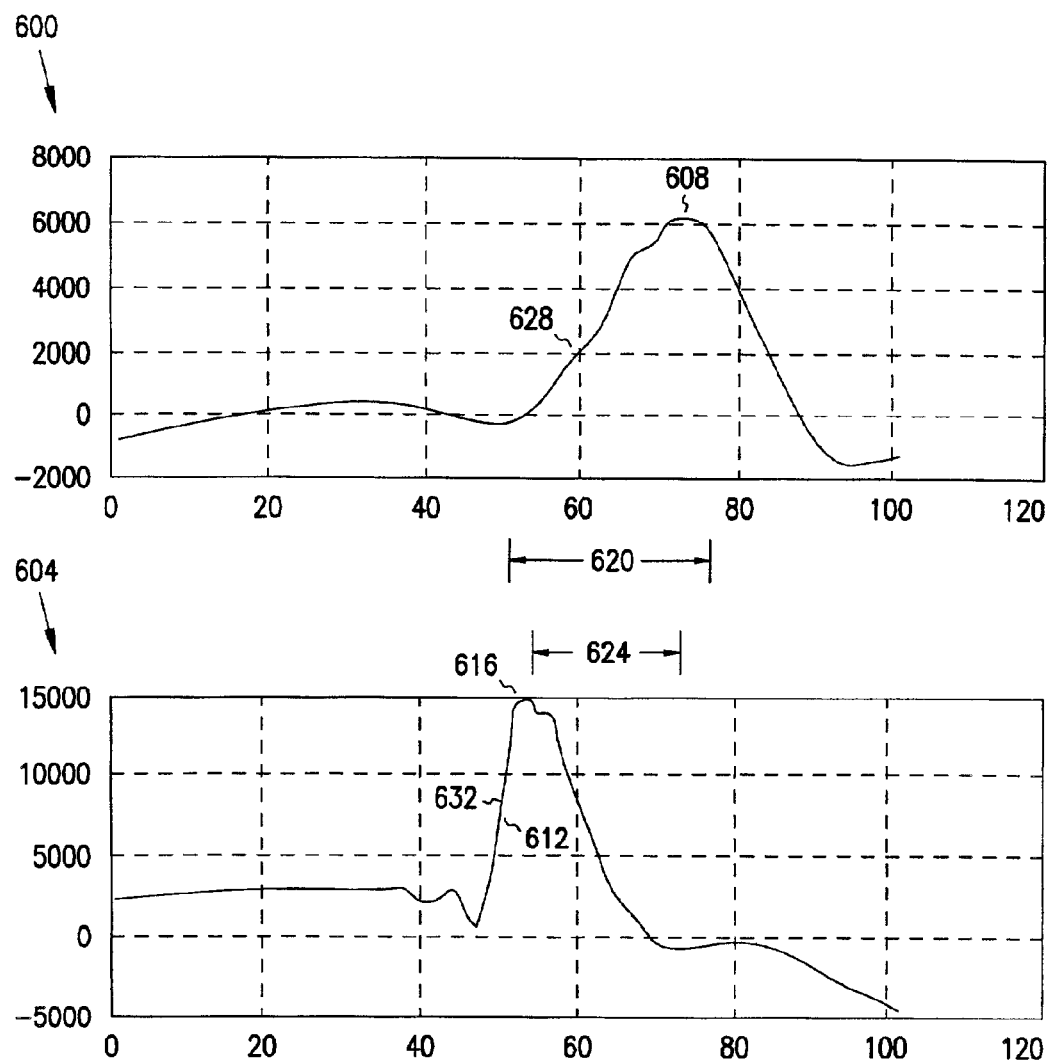
FIG. 6 is an example of a far-field signal and a near-field signal from an arrhythmic complex.

Referring now to FIG. 6 there is shown an embodiment a cardiac complex sensed during a tachycardia episode. FIG. 6 shows one embodiment of a first cardiac signal 600 and a second cardiac signal 604 of a QRS-cardiac complex sensed during a ventricular tachycardia. The first cardiac signal 600 is an example of a far-field cardiac signal, and the second cardiac signal 604 is an example of a near-field cardiac signal sensed using the same electrodes used to sense the far-field cardiac signal of the first cardiac signal 500 and the near-field signal of the second cardiac signal 502.

In addition to using the same electrodes to sense the cardiac signals, the same selection criterion that were used in determining the timing template and the feature template for the normal sinus rhythm complexes are also used on the cardiac complexes sensed during the tachycardia episode. In one embodiment, the selection criterion is the maximum point of the QRS-cardiac complex. FIG. 6 shows the maximum deflection point of the cardiac signal at approximately 608 for the first cardiac signal 600 and 616 for the second cardiac signal 604. In one embodiment, a time difference 624 is determined between the maximum deflection point 608 for the first cardiac signal and the maximum deflection point 616 for the second cardiac signal. In an additional embodiment, a fiducial point 612 is shown on the second cardiac signal 604, where the timing difference 620 between the first cardiac signal 600 and the second cardiac signal 604 is taken between the fiducial point 612 and the maximum deflection point 616 along the first cardiac signal 600.

Figure 7:
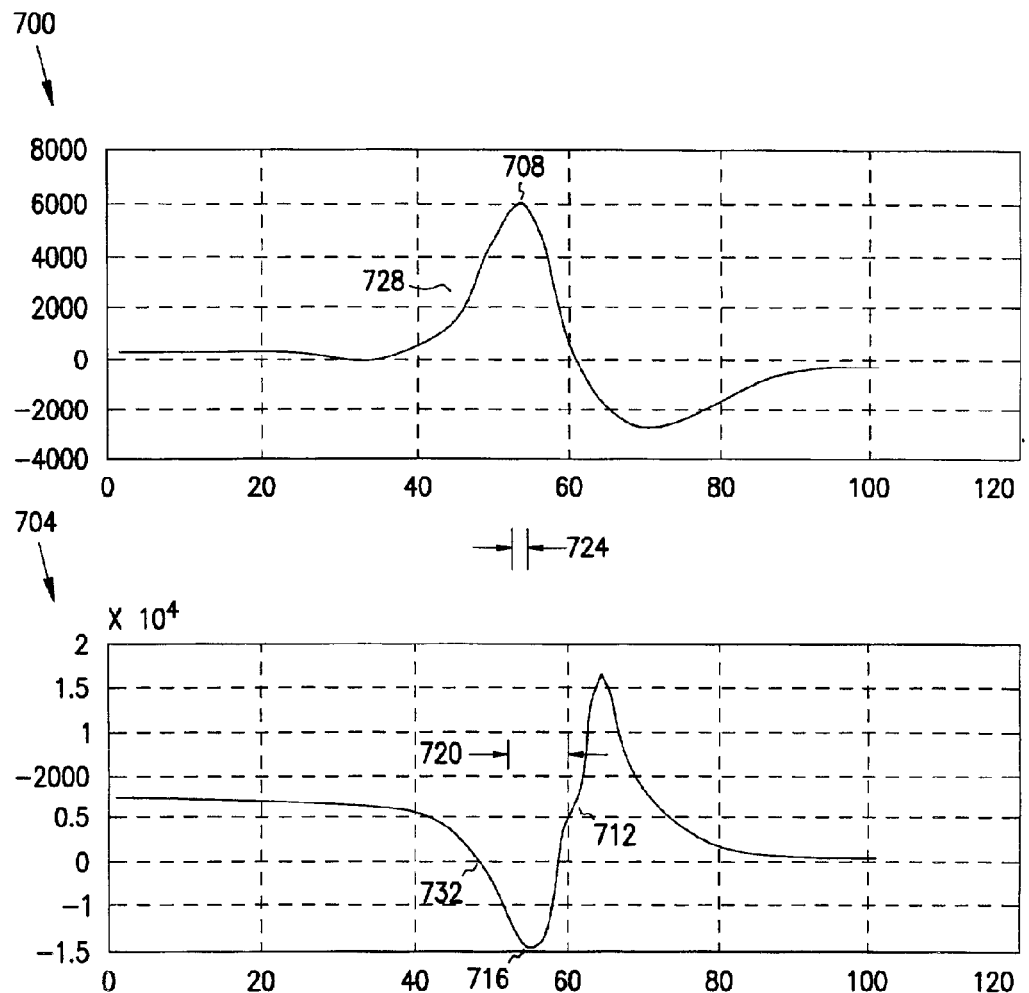
FIG. 7 is an example of a far-field signal and a near-field signal from an arrhythmic complex.

Referring now to FIG. 7 there is shown an embodiment of a sensed cardiac complex. FIG. 7 shows one embodiment of a first cardiac signal 700 and a second cardiac signal 704 of a QRS-cardiac complex sensed during a ventricular tachycardia. The first cardiac signal 700 is an example of a far-field cardiac signal, and the second cardiac signal 704 is an example of a near-field cardiac signal sensed using the same electrodes used to sense the far-field cardiac signal of the first cardiac signal 500 and the near-field signal of the second cardiac signal 502.

In addition to using the same electrodes to sense the cardiac signals, the same selection criterion that were used in determining the timing template and the feature template for the normal sinus rhythm complexes are also used on the cardiac complexes sensed during the tachycardia episode. In one embodiment, the selection criterion is the maximum point of the QRS-cardiac complex. FIG. 7 shows the maximum deflection point of the cardiac signal at approximately 708 for the first cardiac signal 700 and 716 for the second cardiac signal 704. In one embodiment, a time difference 724 is determined between the maximum deflection point 708 for the first cardiac signal and the maximum deflection point 716 for the second cardiac signal. In an additional embodiment, a fiducial point 712 is shown on the second cardiac signal 704, where the timing difference 720 between the first cardiac signal 700 and the second cardiac signal 704 is taken between the fiducial point 712 and the maximum deflection point 708 along the first cardiac signal 700.

The cardiac complex sensed in FIG. 6 is a ventricular tachycardia complex. The cardiac complex sensed in FIG. 7 is a supraventricular tachycardiac complex. As FIGS. 6 and 7 show, there is a notable difference in the time difference for ventricular tachycardia complexes and supraventricular tachycardia complexes. In comparing time differences 624 and 724 to 526, the value of time difference 724 is closer to the value of time difference 528 than the value or time difference 624. Alternatively, the time differences between 620 and 720 as compared to 524 show that the value of time difference 720 is closer to the value of time difference 524 than the value or time difference 620. In one embodiment, the differences in timing difference values are used to differentiate VT from SVT.

In addition, comparisons of characteristics of cardiac signals are also used to differentiate VT from SVT. Referring again to FIG. 5, the slope 518 of the first cardiac signal 500 and the slope 520 of the second cardiac signal 502 are used to differentiate VT complexes from non-VT complexes. In FIGS. 6 and 7, the corresponding characteristics are also found on the cardiac signals. In FIG. 6, the slope of the first cardiac signal 600 is shown generally along 628 and the slope of the second cardiac signal 604 is shown generally along 632. In FIG. 7, the slope of the first cardiac signal 700 is shown generally along 728 and the slope of the second cardiac signal 704 is shown generally along 732. Comparing the characteristics of the sensed cardiac signal in FIGS. 5, 6 and 7 shows that there are once again discernable differences in the signal characteristics. In one embodiment, the slopes shown in FIGS. 5 and 7 are considerably more similar that the slopes shown in FIGS. 5 and 6. These differences allow for a determination of the origin of the ventricular tachycardia.

Referring again to FIGS. 4A and 4B, if the cardiac complex of the tachycardia episode is not categorized as a ventricular tachycardiac complex at 440 based on a comparison of time difference or a signal characteristic, the cardiac complex is analyzed using at least one additional classification procedure. This is necessary to rule out VT that may appear similar to NSR based on a small number of features. In one embodiment, the additional classification procedure is used to classify cardiac signals sensed during the tachycardia episode as either VT complex or non-VT complex.

After making a determination as to whether a cardiac complex is a VT or a non-VT complex, a percentage of ventricular tachycardia complexes is determined at 448. At 452, the calculated percentage of the ventricular tachycardia is compared to a predetermined percentage threshold. In one embodiment, therapy for treating a ventricular tachycardia is applied to the patient's heart at 456 when the percentage of ventricular tachycardia complexes exceeds the predetermined percentage threshold. If the percentage of ventricular tachycardia does not exceed the predetermined percentage threshold, the system returns to 420. In one embodiment, a plurality of cardiac complexes are sampled and categorized for a ventricular tachycardia. In one embodiment, the predetermined percentage threshold is a programmable value in the range of 40 to 60 percent, where a value of approximately 50 percent is an acceptable value.

Figure 8A:
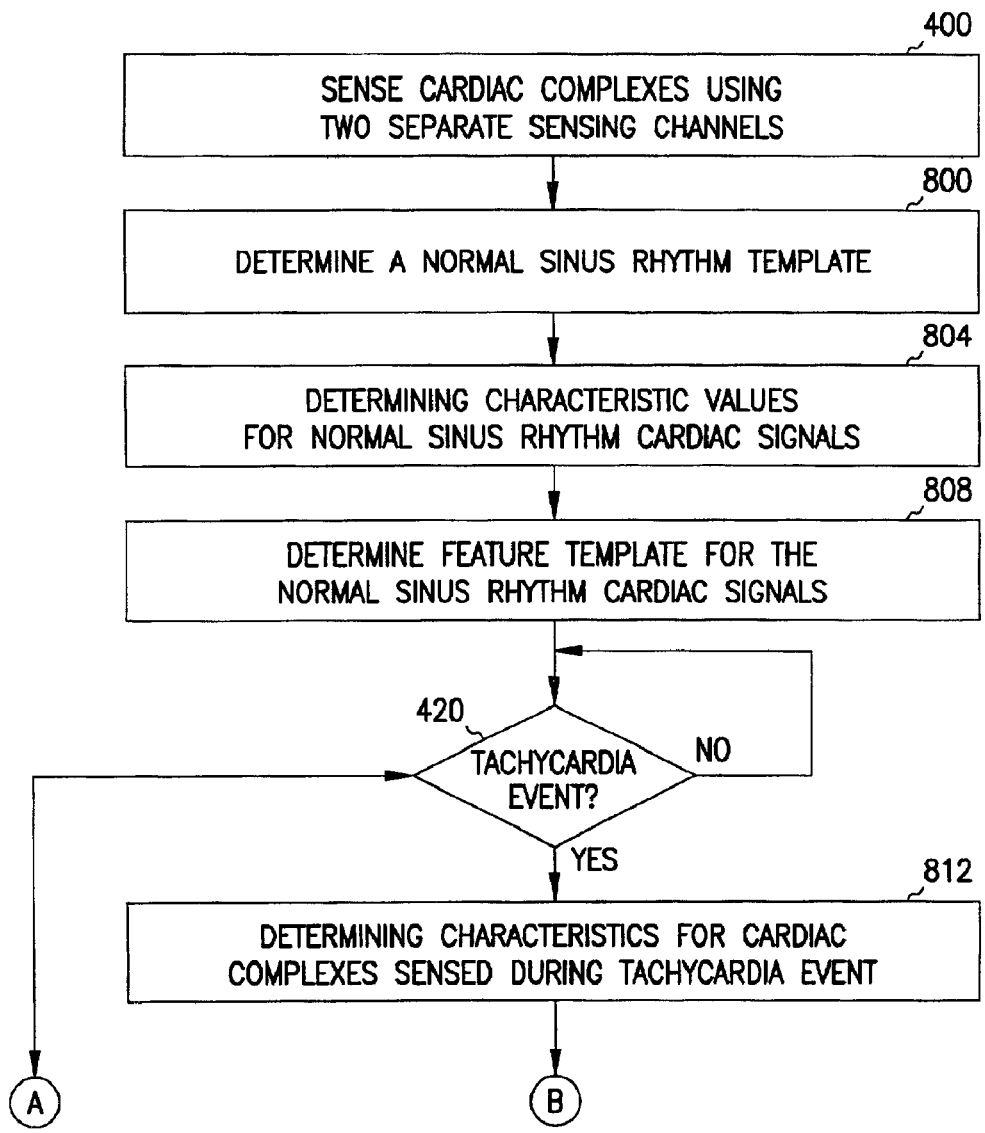
FIGS. 8A and 8B are a flow diagram illustrating one embodiment of the present system.
Figure 8B:
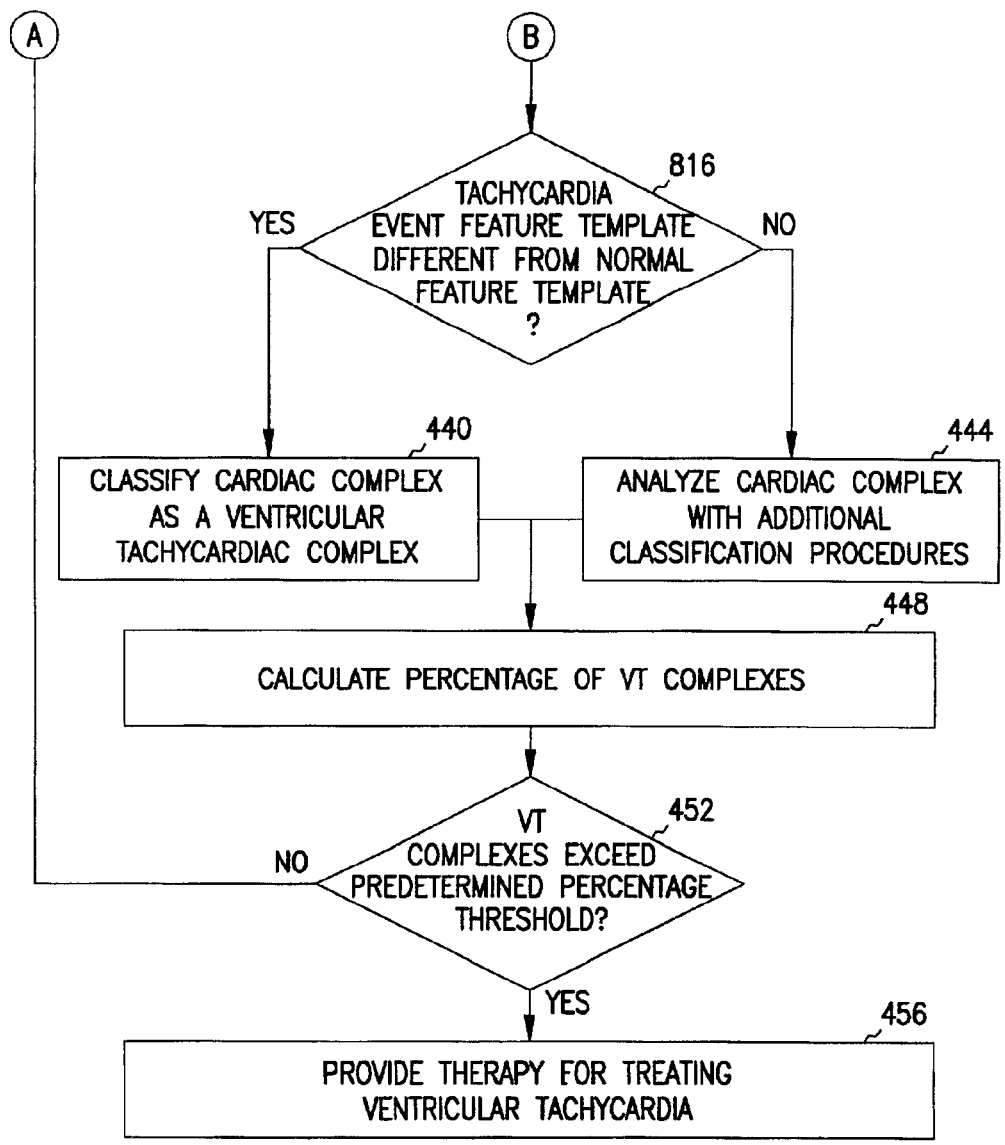

Referring now to FIGS. 8A and 8B, there is shown an alternative embodiment of the present system for distinguishing VT from SVT during a tachycardia episode. In one embodiment, cardiac complexes are sensed at 400 as previously discussed. At 800, the sensed cardiac complexes are used to determine or calculate a normal sinus rhythm template, or a model, against which cardiac signals sensed during a tachycardia episode are compared. At 800, the template is determined from characteristics of the sensed cardiac signals sensed during normal sinus rhythm. In one embodiment, the characteristic of the sensed cardiac signal is the slope of a predetermined portion of the cardiac signal. In an additional embodiment, the characteristic used to create the template is the amplitude of a maximum deflection point (point along the sensed signal having the maximum absolute value) of the cardiac signal, such as a maximum or minimum point along either the first cardiac signal or the second cardiac signal. In an alternative embodiment, the characteristic is the slew rate of the cardiac signals sensed during normal sinus rhythm.

At step 804 the characteristic values for the normal sinus rhythm cardiac complexes are determined by the system. The feature template is derived from the characteristics of the sensed cardiac complexes. In one embodiment, the feature template is a median signal amplitude of one or more features on the cardiac complexes sensed during normal sinus rhythm. In one embodiment, the medical device system senses complexes during normal sinus rhythm and determines a median signal amplitude for the first feature and the second feature from a plurality of normal sinus rhythm complexes. In one embodiment, the median signal amplitude for the first feature is determined relative a baseline signal of the first signal and the median signal amplitude for the second feature is determined relative a baseline signal of the second signal. In one embodiment, median signal amplitudes are computed from five (5) or more cardiac complexes sensed during normal sinus rhythm. In one embodiment, the five (5) or more cardiac complexes are cardiac complexes signals sequentially sensed during normal sinus rhythm. In one embodiment, if the variability in the median signal amplitude calculated during normal sinus rhythm is greater than or equal to approximately 20 percent, the median signal amplitude is redetermined.

When the medical device system encounters a tachycardia episode, a signal amplitude of the first feature point and the second feature point for each cardiac complex is determined. In one embodiment, the signal amplitude for the first feature and the second feature are calculated relative the baseline signal of the first signal and the second signal respectively. The signal amplitude of the first feature point and the second feature point are then compared to the corresponding median signal amplitude of the first feature point and the second feature point, and if the signal amplitude of at least one of the first feature and the second feature exceeds the corresponding median signal amplitude of the first feature and the second feature by a predetermined amount, the cardiac complex is characterized as a ventricular tachycardia complex.

Other features of the first signal and the second signal are also useful in determining whether a cardiac complex is a ventricular tachycardiac complex. In one embodiment, the medical device system senses the first signal representative of electrical activity at a first cardiac region, where the first signal includes a QRS-complex representative of a cardiac cycle. The medical device system also senses the second signal representative of electrical activity at a second cardiac region, where the second signal including the QRS-complex as sensed in the second cardiac region. Initially, a representative slope value for both the first signal and the second signal is determined from a plurality of normal sinus rhythm complexes. In one embodiment, the representative slope value is a median slope value determined from the plurality of normal sinus rhythm complexes.

During a tachycardia episode, the medical device system senses cardiac signals (e.g., QRS-cardiac complexes) and determines a first slope for the first signal and a second slope for the second signal. In one embodiment, the both the first signal and the second signal are maximum slopes for both the first signal and the second signal. The medical device system then compares the maximum slope of the first signal and the second signal of the QRS-cardiac complex to the corresponding representative slope for the first signal and the second signal. Based on this comparison, if the slope of at least one of the first signal and/or the second signal deviates from the corresponding representative slope for the first signal and the second signal by a predetermined amount, the cardiac complex is characterized as a ventricular tachycardia complex.

At 420 cardiac complexes are sensed to determined the onset of a tachycardia episode. If no tachycardia episode is sensed, the system continues to sense cardiac signals and analyzes them for the occurrence of a tachycardia episode. In one embodiment, the occurrence of a tachycardia episode is based on the cardiac rate, where a tachycardia episode is declared when the cardiac rate exceeds a predetermined threshold. In one embodiment, the predetermined threshold is a cardiac rate of between 150 and 180 beats per minute. Other systems of determining the occurrence of a tachycardia episode are known and are considered to be within the scope of the present system.

When a tachycardia episode is detected the system then proceeds to 812. At 812, cardiac complexes from the tachycardia episode are sensed and characteristics from the sensed cardiac complexes are determined. The characteristics determined on the cardiac complexes of the tachycardia episode are the corresponding characteristics that were detected in the cardiac complexes during normal sinus rhythm. In other words, the characteristics that were used in determining the feature template during normal sinus rhythm are the characteristics that are extracted from the cardiac signals sensed during the ventricular tachycardia episode.

In one embodiment, the determination of whether a QRS-cardiac complex of a tachycardia episode is a VT complex or a SVT complex is based on a comparison of characteristic values and the feature template. When the medical device encounters a tachycardia episode, characteristic values for each QRS-cardiac complex sensed during the tachycardia episode is determined. In one embodiment, the medical device system determines the characteristic value for the first feature on the first signal and the second feature on the second signal of the QRS-cardiac complex at 816. The characteristic values of the QRS-cardiac complex is then compared to the feature template calculated for normal sinus rhythm at 808. Based on the comparison, if the characteristic values of the cardiac complex exceeds the feature template by a predetermined margin, the cardiac complex is characterized as a ventricular tachycardia complex at 440. In one embodiment, a ventricular tachycardiac complex is a cardiac complex that is characteristic of the occurrence of the ventricular tachycardia episode. In other words, the ventricular tachycardiac complex is a cardiac complex that makes up the occurrence of the ventricular tachycardiac episode.

When the cardiac complex of the tachycardia episode is not categorized as a ventricular tachycardiac complex at 816, the cardiac complex is analyzed using at least one additional classification procedure at 444. In one embodiment, the additional classification procedure is used to classify cardiac signals sensed during the tachycardia episode as either VT complex or non-VT complex.

After making a determination as to whether a cardiac complex is a VT or a SVT complex, a percentage of ventricular tachycardia complexes is determined at 448. At 452, the calculated percentage of the ventricular tachycardia is compared to a predetermined percentage threshold. In one embodiment, therapy for treating a ventricular tachycardia is applied to the patient's heart at 456 when the percentage of ventricular tachycardia complexes exceeds the predetermined percentage threshold. If the percentage of ventricular tachycardia does not exceed the predetermined percentage threshold, the system returns to 420. In one embodiment, a plurality of cardiac complexes are sampled and categorized for a ventricular tachycardia. In one embodiment, the predetermined percentage threshold is a programmable value in the range of 40 to 60 percent, where a value of approximately 50 percent is an acceptable value.

Figure 9:
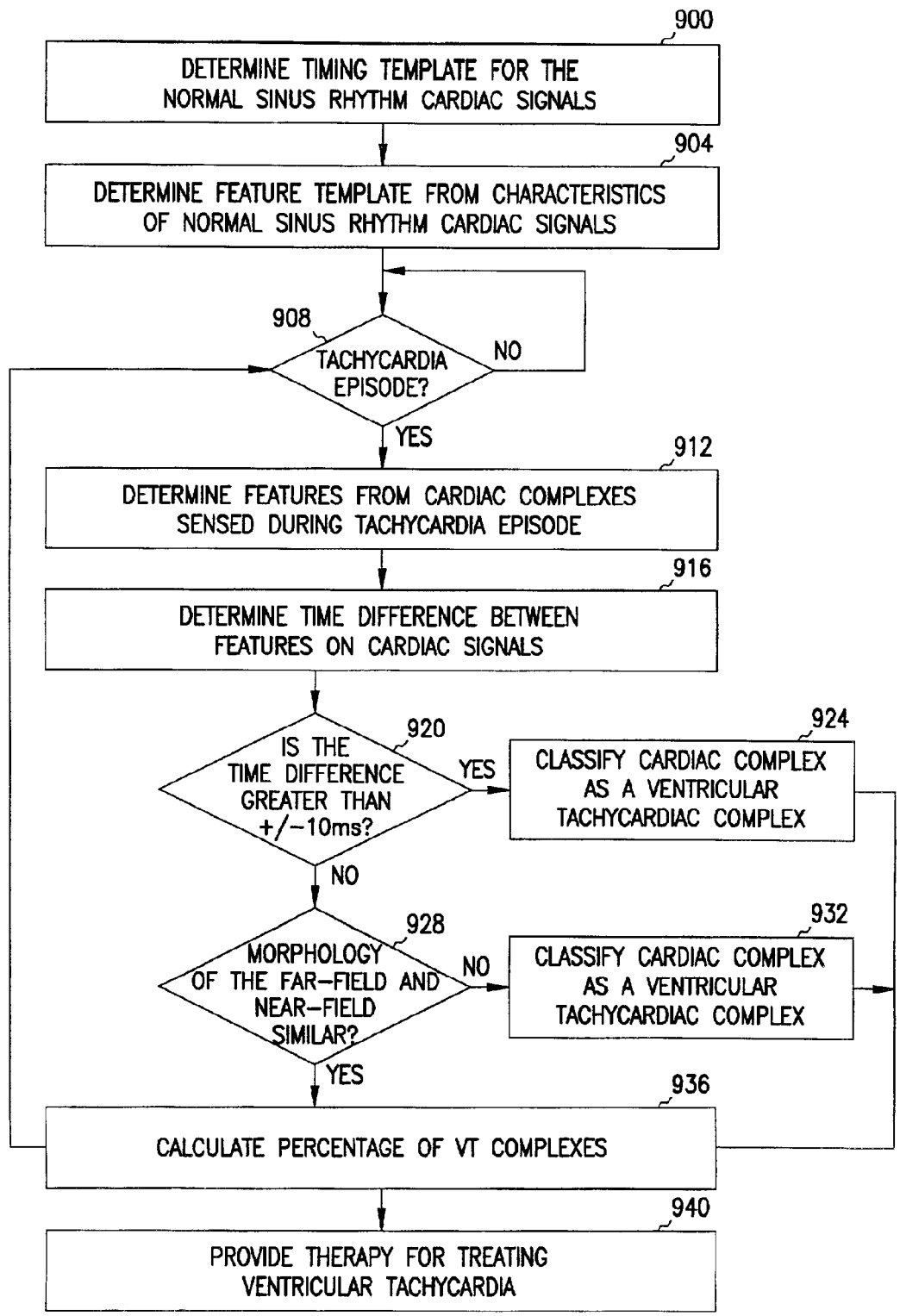
FIG. 9 is a flow diagram illustrating one embodiment of the present system.

Referring now to FIG. 9, there is shown an alternative embodiment of the present system. At step 900 a timing template is determined for normal sinus rhythm signals. The timing template can be determined as previously discussed. In the present embodiment, the timing template is determined using the time difference between the absolute maximum deflection point along a far-field signal and the fiducial point along a near-field signal. At 904, a feature template is also determined. The feature template can be computed as previously discussed.

Cardiac complexes are then sensed at 908 to determine when the heart has entered a tachycardia episode. If the heart enters into a tachycardia episode, the system proceeds to 912. At 912, the timing difference between the absolute maximum deflection point along a far-field signal and the fiducial point along a near-field signal is taken for the sensed cardiac complex. At 916, feature values are derived from the far-field signal and the near-field signal for the sensed cardiac complex. The system then proceeds to 920 where the timing difference of the cardiac complex sensed during the tachycardia episode is compared to the timing template. If the timing difference is greater than about a predetermined threshold (e.g., 10 milliseconds), the cardiac complex is classified as VT complex at 924. If the timing difference is not greater than about +/−10 milliseconds, the system then proceeds to 928 where the morphology of the far-field signal and the near-field signal are used to determined whether the cardiac complex is a VT complex or a SVT complex. Some methods useful for comparing morphologies of cardiac complexes in two or more cardiac signals are presented in U.S. patent application Ser. No. 09/249,128, entitled "System and Method for Classifying Cardiac Complexes" which is filed on the same day as the instant U.S. Patent application and that is hereby incorporated by reference in its entirety.

In one embodiment, at 928 morphology of the far-field signals and/or the near-field signals of the unknown cardiac complex are compared to a representative normal sinus rhythm complex in a comparison window to determine whether the unknown cardiac complex is a VT complex or a SVT complex. In one embodiment, the representative normal sinus rhythm complex includes a first normal sinus rhythm (NSR) representative complex and a second NSR representative complex determined from the plurality QRS-cardiac complexes sensed during normal sinus rhythm. In one embodiment, the template generator 240 determines the first and second NSR representative complexes. In one embodiment, the morphologies of the first signal (the far-field signal) and the second signal (the near-field signal) for the unknown cardiac complex are compared to the morphologies of the first NSR representative complex (a far-field signal in this example) and the second NSR representative complex (a near-field signal in this example) of the representative normal sinus rhythm complex in the comparison window. From the morphology comparison of the cardiac complex sensed in the first signal to the morphology of the first NSR representative complex and the morphology of the cardiac complex sensed in the second signal to the morphology of the second NSR representative complex the cardiac complex can be classified as either a VT complex or a SVT complex.

In an alternative embodiment, before a morphology comparison is made between the cardiac complex sensed in the first signal or the second signal (e.g., the near-field or far-field signals) of the unknown cardiac complexes and the first NSR representative complex and a second NSR representative complex, the cardiac complex sensed in the first signal and the second signal and the first and second NSR representative complexes are positioned in a comparison window. In one embodiment, the comparison window isolates an individual cardiac complex as sensed in the first signal and the second signal, where the first signal and the second signal of the cardiac complex are positioned relative to each other based on their time of occurrence (i.e., the x-axis of the cardiac complex plot has the units of time on which the relative occurrence of the cardiac complex sensed in the first signal and the second signal are plotted). Within the comparison window, the cardiac complex sensed in the first signal and the first NSR representative complex are aligned around a predetermined feature that is common to both cardiac complexes. In one embodiment, the signal feature comparison circuit 238 aligns the unknown cardiac complex and the representative NSR complex around the predetermined feature. After the representative NSR complex and the unknown cardiac complex have been aligned around the predetermined feature the morphology of the cardiac complex sensed in the second signal is then compared to the second NSE representative complex to allow the unknown cardiac complex to be classified as either a VT complex or an SVT complex. In one embodiment, the morphology analyzer circuit 248 compares the morphology of the unknown cardiac complex to determine whether the tachycardia complex is a ventricular tachycardia complex.

Figure 10:
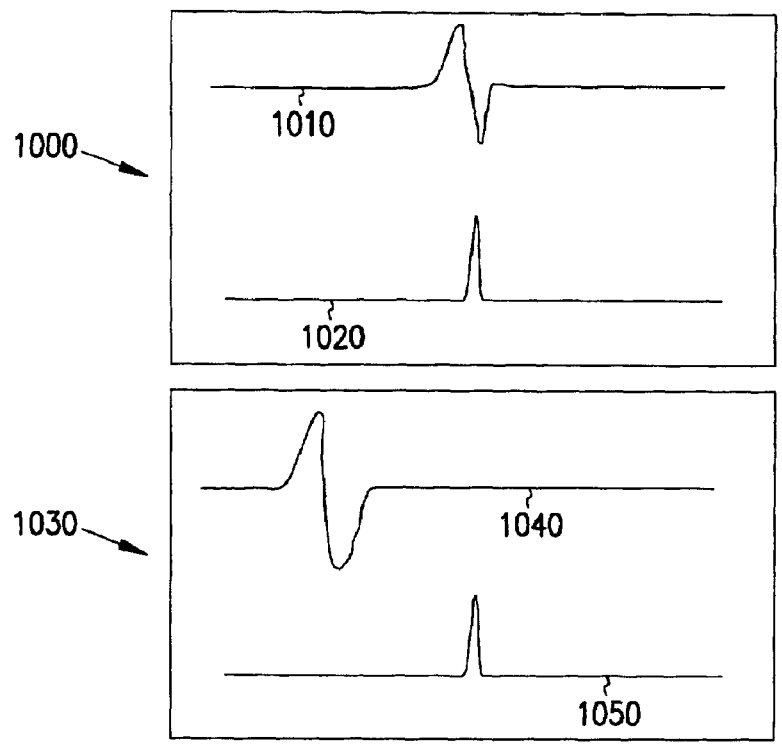
FIG. 10 is one embodiment of a first signal and a second signal of a cardiac complex and a first signal and a second signal of a normal sinus rhythm complex, where the first signal of the cardiac complex and the first signal of the normal sinus rhythm complex are aligned.

FIG. 10 shows one embodiment of aligning an unknown cardiac complex with a NSR representative complex in a comparison window. In one embodiment, the NSR representative complex is an average or a median NSR complex generated from NSR complexes sensed with the implantable medical device. A NSR representative complex is shown at 1000, where 1010 represents a first NSR representative complex (a far-field signal in this example) and 1020 represents a second NSR representative complex (a near field signal in this example). An unknown cardiac complex is shown in 1030, where 1040 represents the first signal (a far-field signal) and 1050 represents the second signal (a near field signal) of the unknown cardiac complex.

The second features of both the unknown cardiac complex and the NSR representative complex are first aligned along a predetermined feature that is common in both the cardiac complex sensed in the second signal and the second NSR representative complex. In one embodiment, the maximum deflection point (dV/dt=0) in the near-field signals is used as the predetermined feature (or reference point) around which to align the unknown cardiac complex and the representative normal sinus rhythm complex. Other feature points on the near-field signals can also be used to align the unknown cardiac complex and the representative normal sinus rhythm complex. Once the second signals (near-field signals) have been aligned (i.e., located at the same point in the comparison window), the morphology of the first signal (far-field signal) and the morphology of the first representative NSR signal (far-field signal) can then be compared to determine whether the unknown cardiac complex is similar (SVT) or dissimilar (VT) with respect to a predetermined threshold. By first aligning the cardiac complexes, the relative time of occurrence of the far-field signals is used to further accentuate any morphological differences in the two signals being compared.

Figure 11:
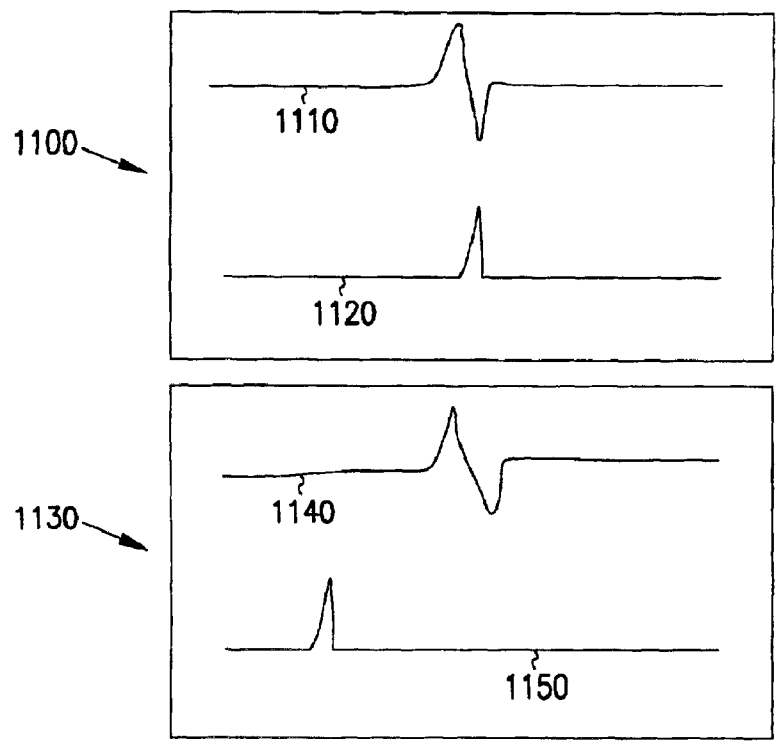
FIG. 11 is one embodiment of a first signal and a second signal of a cardiac complex and a first signal and a second signal of a normal sinus rhythm complex, where the second signal of the cardiac complex and the second signal of the normal sinus rhythm complex are aligned.

FIG. 11 shows an additional embodiment of aligning an unknown cardiac complex with a representative normal sinus rhythm complex. A NSR representative complex is shown at 1100, where 1110 represents the first NSR representative complex (a far-field signal) and 1120 represents the second NSR representative complex (a near field signal). An unknown cardiac complex is shown in 1130, where 1140 represents the first signal (a far-field signal) and 1150 represents the second signal (a near field signal).

In the present embodiment, the first features of both the unknown cardiac complex and the NSR representative complex are taken as the predetermined feature around which to align the cardiac complex in the first signal and the first NSR representative complex. In one embodiment, the maximum deflection point (dV/dt=0) in the far-field signals is used as the first feature (or reference point) around which to align the unknown cardiac complex and the NSR representative complex. Other feature points on the far-field signals can also be used to align the unknown cardiac complex and the representative normal sinus rhythm complex. Once the first signals (far-field signals) have been aligned, the morphology of the second signal (near-field signal) and the morphology of the second representative NSR signal (near-field signal) can then be compared to determine whether the unknown cardiac complex is a VT complex or an SVT complex. By first aligning the cardiac complexes, the relative time of occurrence of the far-field signals is used to further accentuate any morphological differences in the two signals being compared.

In one embodiment, the morphology of the far-field and/or near-field signals is compared using a correlation waveform analysis, as is known in the art. The correlation waveform analysis is a method of comparing two waveforms to determine how similar they are to one another, where being similar indicates SVT and being dissimilar indicates VT. Correlation waveform analysis uses a correlation coefficient between a template of sinus rhythm and the unknown complex under analysis. The correlation coefficient for each unknown complex falls between −1 and 1, where 1 indicates a perfect match between the unknown complex and the template. In addition to correlation waveform analysis, other morphology comparison methods or methods of classifying unknown cardiac complexes can be used to distinguish VT complex from SVT complex once the unknown cardiac complex is aligned around a common feature with a representative normal sinus rhythm complex.

After making a determination as to whether a cardiac complex is a VT or a non-VT complex, a percentage of ventricular tachycardia complexes is determined at 936. At 936, the calculated percentage of the ventricular tachycardia is compared to a predetermined percentage threshold. In one embodiment, therapy for treating a ventricular tachycardia is applied to the patient's heart at 936 when the percentage of ventricular tachycardia complexes exceeds the predetermined percentage threshold. If the percentage of ventricular tachycardia does not exceed the predetermined percentage threshold, the system returns to 908. In one embodiment, the predetermined percentage threshold is a programmable value in the range of 40 to 60 percent, where a value of approximately 50 percent is an acceptable value. Once the percentage of VT complexes exceeds the predetermined percentage threshold the system then delivers appropriate therapy at 940 to treat the ventricular tachycardia.

In an additional embodiment, it is possible to use three or more cardiac sensing channels to classify an tachycardiac complex as either a VT complex or an SVT complex. For example, cardiac sensing channels can include a far-field channel and a near-field channel sensed in and around the right atrial and ventricular chambers of the heart as previously described. In addition, a far-field or a near-field channel sensed at a location adjacent to the left ventricular chamber can also be used in classifying a tachycardiac complex as either a VT complex or an SVT complex.

Figure 12:
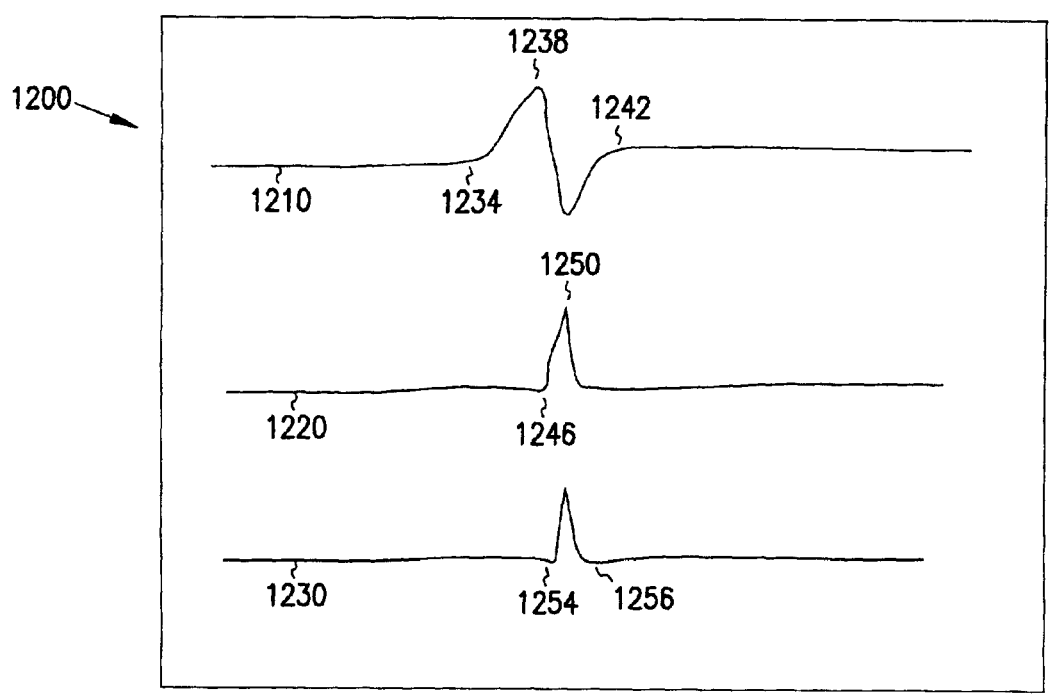
FIG. 12 is an example of a plurality of sensing channels useful in one embodiment of the present system.

FIG. 12 shows one embodiment of three sensing channels being used to detect a cardiac complex. In one embodiment, a third signal representative of electrical activity at a third cardiac region is sensed, where the third signal includes a QRS-cardiac complex representative of a cardiac cycle sensed in the third cardiac region. A cardiac complex sensed with three sensing channels is shown at 1200. In one embodiment, the first sensing channel 1210 is detecting right ventricular far-field signals; the second sensing channel 1220 is detecting right ventricular near-field signals; and the third sensing channel 1230 is detecting a left ventricular near-field signal. In one embodiment, the third sensing channel is sensed from a position that is adjacent the left ventricular chamber of the heart.

A comparison template is created from feature values and/or timing differences between features from sensed normal sinus rhythm complexes. In one embodiment, the comparison template has a plurality of values derived from one or more features on the first signal, the second signal and the third signal of the normal sinus rhythm complexes. In one embodiment, the plurality of values includes a series of timing differences and/or feature values derived from any combination of the sensed cardiac signals. In one embodiment, the template generator 240 generates the comparison template from cardiac complexes sensed during normal sinus rhythm.

The timing differences and/or features used in developing a comparison template are programmable parameters in the implantable medical device. To create the comparison template, one or more features are selected on the first signal, the second signal and the third signal. The features are selected based on the selection criterion previously discussed. Once the features have been selected and the way in which the features are to be used in the comparison template defined (e.g., used to generate timing differences or used to generate feature values), the comparison template is generated from a plurality of sensed normal sinus rhythm complexes. In one embodiment, the values calculated for the comparison template are average values of the sensed normal sinus rhythm complexes. Alternatively, the values calculated for the comparison template are median values of the sensed normal sinus rhythm complexes.

As unknown cardiac complexes are sensed, the corresponding plurality of values determined from the normal sinus rhythm complexes to create the comparison template are determined from the one or more features on the first signal, the second signal and the third signal of the cardiac complex. The plurality of values derived from the cardiac complex is then compared to the comparison template. When one or more of the plurality of values of the cardiac complex exceed the corresponding value in the comparison template by a predetermined margin, the control system characterizes the cardiac complex as a VT complex.

In one embodiment, the plurality of values are derived from timing differences between the one or more features on the first signal, the second signal and the third signal. For example, an not by way of limitation, a six value comparison template can be generated by taking the timing differences between a series of features along any combination of the right ventricular far-field signal 1210, the right ventricular near-field signal 1220 and/or the left ventricular near-field signal 1230. In one embodiment, the comparison template is created by (1) taking the timing differences between the start of the right ventricular far-field signal 1210, shown at 1234, and the maximum deflection point along the right ventricular far-field signal 1210, shown at 1238; (2) taking the timing differences between the maximum deflection point 1238 and the end of the right ventricular far-field signal 1210, shown at 1242; (3) taking the timing differences between the start of the right ventricular far-field signal 1234 and the start of the right ventricular near-field signal 1220, shown at 1246; (4) taking the timing differences between the start of the right ventricular near-field signal 1246 and the maximum deflection point of the right ventricular near-field signal 1220, shown at 1250; (5) taking the timing differences between the maximum deflection point of the right ventricular near-field signal 1250 and the start of the left ventricular near-field signal 1230, shown at 1254; and (6) taking the timing differences between the start of the left ventricular near-field signal 1254 and the end of the left ventricular near-field signal 1230, shown at 1256.

In this embodiment, the comparison template has six values, which are derived from timing differences between features along a plurality of cardiac sensing channel. Once the comparison template has been generated from sensed normal sinus rhythm complexes, the same timing differences are taken along the same three sensing channels for unknown cardiac complexes and the resulting six values are compared to the comparison template. Based on the timing differences between the six values, cardiac complexes are classified as either VT complexes or SVT complexes.

Alternatively, comparison templates can be generated from a first signal and a second signal. In this embodiment, one or more features, based on the selection criterion, are selected for the first signal and the second signal. The comparison template is then created from normal sinus rhythm complexes, where the comparison template has a plurality of values derived from the one or more features on the first signal and the second signal of the normal sinus rhythm complexes. In one embodiment, the plurality of values can include timing differences between features on either the first signal and/or the second signal. Alternatively, the plurality of values can include feature values on either the first signal and/or the second signal. Combinations of feature values and timing differences are also possible.

As unknown cardiac complexes are sensed, the corresponding plurality of values determined from the normal sinus rhythm complexes to create the comparison template are determined from the one or more features on the first signal and the second signal. The plurality of values derived from the cardiac complex is then compared to the comparison template. When one or more of the plurality of values of the cardiac complex exceed the corresponding value in the comparison template by a predetermined margin, the cardiac complex is characterized as a VT complex.

In addition, one or more of the positions in a comparison template can also have a weighting factor associated with it. The weighting factor, or factors, allow one or more of the individual values within the comparison template to have more, or less, influence on the decision to classify a cardiac complex as either a VT complex or an SVT complex. For example, when a particular timing difference or feature value in a patient's sensed cardiac signal is known to be indicative of a particular cardiac condition (e.g., VT or SVT), more weight can be given to that position in the comparison template as compared to any other position in the comparison template. So, when the more heavily weighted timing difference or feature value in the comparison template exceeds the predetermined minimum value, the system can classify the cardiac complex regardless of what the other timing differences or feature values in the template indicate. In addition, the weightings can be predetermined from patient population studies and research on individual patients.

In addition to using three cardiac channels in developing the comparison template, it is also possible to use four or more cardiac channels in developing the comparison template. Other channels that are useful include those sensing cardiac complexes from the housing of the implantable medical device or atrial near-field or far-field channels, just as examples. Other combinations of sensing channels are possible and considered within the present subject matter.

We claim:

1. A method, comprising:
   sensing a first cardiac complex of a heart contraction at a first cardiac region of a patient;
   sensing a second cardiac complex, associated with the same heart contraction as the first cardiac complex, at a second cardiac region of said patient;
   selecting a first fiducial feature of the first cardiac complex;
   selecting a second fiducial feature of the second cardiac complex;
   determining a time difference between the first and second fiducial features;
   comparing the time difference to a template time difference between the first and second fiducial features obtained from said patient during normal sinus rhythm; and
   if the time difference differs from the template time difference by at least a predetermined margin, characterizing the first and second signals as arrhythmic.

2. The method of claim 1, further including:
   if the time difference exceeds the template time difference by at least a predetermined margin, characterizing the heart contraction as a tachycardia heart contraction;
   determining a percentage of tachycardia heart contractions in a plurality of heart contractions; and
   when the percentage of tachycardia heart contractions exceeds a threshold, delivering therapy for treating the tachycardia.

3. The method of claim 1, wherein the first and second fiducial features include at least one of:
   a predetermined signal deviation from a baseline representing a beginning of the cardiac complex;
   a maximum deflection of the cardiac complex;
   a signal return to the baseline within a predetermined time window from the beginning of the cardiac complex, the signal return representing an end of the cardiac complex; and
   a maximum slope portion of the cardiac complex.

4. The method of claim 1, wherein the template time difference is obtained from said patient using the time differences determined for a plurality of heart contractions during normal sinus rhythm.

5. A method, comprising:
   sensing a first cardiac complex at a first cardiac region during a cardiac cycle of a patient;
   sensing a second cardiac complex at a second cardiac region during the cardiac cycle;
   selecting a first fiducial feature of the first cardiac complex;
   selecting a second fiducial feature of the second cardiac complex;
   determining a first amplitude for the first fiducial feature relative to a baseline of the first cardiac complex;
   determining a second amplitude for the second fiducial feature relative a baseline of the second cardiac complex;
   comparing the first and second amplitudes to respective first and second thresholds obtained from said patient during normal sinus rhythm; and
   characterizing whether the first and second cardiac complexes are arrhythmic using the results of the comparison.

6. The method of claim 5, further comprising:
   determining the first threshold using a statistical value obtained from the first amplitudes over a plurality of cardiac cycles during normal sinus rhythm; and
   determining the second threshold using a statistical value obtained from the second amplitudes over a plurality of cardiac cycles during normal sinus rhythm.

7. The method of claim 5, wherein the characterizing includes:
   if the first amplitude differs from the first threshold by at least a predetermined amount, characterizing the cardiac complex as arrhythmic; and
   if the second amplitude differs from the second threshold by at least the predetermined amount, characterizing the cardiac complex as arrhythmic.

8. The method of claim 5, wherein the first and second fiducial features include at least one of:
   a predetermined signal deviation from a baseline representing a beginning of a cardiac complex;
   a maximum deflection of a cardiac complex;
   a signal return to the baseline within a predetermined time window from the beginning of a cardiac complex, the signal return representing an end of the cardiac complex; and
   a maximum slope portion of a cardiac complex.

9. A method, comprising:
   sensing a first cardiac complex at a first cardiac region of a patient during a cardiac cycle;
   sensing a second cardiac complex, associated with the same heart contraction as the first cardiac complex, at a second cardiac region during the cardiac cycle;
   determining a first slope of a portion of the first cardiac complex;
   determining a second slope of a portion of the second cardiac complex;
   comparing the first slope to a first threshold slope and comparing the second slope to a second threshold slope, the first and second threshold slopes obtained from said patient during normal sinus rhythm; and
   characterizing whether the first and the second signals are arrhythmic using the results of the comparison.

10. The method of claim 9, wherein the first slope is a maximum slope along the first cardiac complex during the cardiac cycle, and the second slope is the maximum slope along the second cardiac complex during the cardiac cycle.

11. The method of claim 9, wherein the first slope is taken along a predetermined first major inflection of the first cardiac complex, and the second slope is taken at a substantially identical predetermined first major inflection of the second cardiac complex.

12. The method of claim 9, further comprising:

determining the first threshold slope over a plurality of cardiac cycles during normal sinus rhythm; and determining the second threshold slope over a plurality of cardiac cycles during normal sinus rhythm.

13. The method of claim 9, wherein the characterizing includes:

if the first slope differs from the first threshold slope by at least a predetermined amount, characterizing the cardiac complex as arrhythmic; and if the second slope differs from the second threshold slope by at least the predetermined amount, characterizing the cardiac complex as arrhythmic.

14. A system, comprising:

a control system including first and second inputs to monitor respective first and second signals, each including the same cardiac complex detected at different cardiac locations of a patient;

a morphology analyzer coupled to the control system, the morphology analyzer adapted to locate a first fiducial feature of a first cardiac complex on the first signal and a second fiducial feature of a second cardiac complex on the second signal, the first and second fiducial features associated with the same heart contraction;

a signal feature comparison circuit coupled to the morphology analyzer, the signal feature comparison circuit adapted to compare at least one characteristic of at least one of the first and second fiducial features to a template quantity obtained from said patient that is representative of a normal sinus rhythm complex; and wherein the control system designates the cardiac complex as arrhythmic when the at least one characteristic differs from the corresponding template time difference by at least a predetermined margin.

15. The system of claim 14, wherein the morphology analyzer includes a characteristic quantity generator, coupled to the signal feature comparison circuit, configured to generate at least one of:

a time difference between the first and second fiducial features;

a first amplitude of the first fiducial feature;

a second amplitude of the second fiducial feature;

a first slope associated with the first signal; and a second slope associated with the second signal.

16. The system of claim 15, further including a template generator, coupled to the signal feature comparison circuit, the template generator adapted to generate the template time differences over a plurality of cardiac complexes obtained from the patient during normal sinus rhythm.

17. The system of claim 14, wherein the morphology analyzer includes an amplitude detector adapted to detect at least one of the first and second fiducial features, and wherein the at least one of the first and second fiducial features includes at least one of:

a signal deviation from a baseline;

a maximum signal deflection;

a signal return to the baseline; and a predetermined major signal inflection.

18. The system of claim 17, wherein the morphology analyzer further includes a timer adapted to determine at least one time of detection of the at least one of the first and second fiducial features.

* * * * *